(12) United States Patent
Chirife et al.

(10) Patent No.: US 8,332,031 B2
(45) Date of Patent: Dec. 11, 2012

(54) SYSTEM AND METHOD OF AV INTERVAL SELECTION IN AN IMPLANTABLE MEDICAL DEVICE

(75) Inventors: Raul Chirife, Acassuso (PY); William J Combs, Minnetonka, MN (US); Russell L. Lundstrom, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 143 days.

(21) Appl. No.: 12/848,769

(22) Filed: Aug. 2, 2010

(65) Prior Publication Data

US 2011/0022108 A1 Jan. 27, 2011

Related U.S. Application Data

(62) Division of application No. 11/257,715, filed on Oct. 25, 2005, now Pat. No. 7,769,449.

(51) Int. Cl.
*A61N 1/00* (2006.01)

(52) U.S. Cl. ............................................. 607/9; 607/25

(58) Field of Classification Search .................. 607/9, 25
See application file for complete search history.

(56) References Cited

U.S. PATENT DOCUMENTS

| | | | |
|---|---|---|---|
| 4,485,813 A | 12/1984 | Anderson et al. | |
| 4,719,921 A | 1/1988 | Chirife | |
| 5,139,020 A * | 8/1992 | Koestner et al. | ................. 607/24 |
| 5,154,171 A | 10/1992 | Chirife | |
| 5,174,289 A * | 12/1992 | Cohen | ............................. 607/9 |
| 5,179,949 A | 1/1993 | Chirife | |
| 5,330,511 A * | 7/1994 | Boute | ............................. 607/25 |
| 7,128,714 B1 | 10/2006 | Antonelli et al. | |

* cited by examiner

*Primary Examiner* — Niketa Patel
*Assistant Examiner* — Joseph Stoklosa
(74) *Attorney, Agent, or Firm* — Reed A. Duthler

(57) ABSTRACT

An implantable medical device provides ventricular pacing capabilities and optimizes AV intervals for multiple purposes. In general, intrinsic conduction is promoted by determining when electromechanical systole (EMS) ends and setting an AV interval accordingly. EMS is determined utilizing various data including QT interval, sensor input, and algorithmic calculations.

13 Claims, 16 Drawing Sheets

SYSTEM AND METHOD OF AV INTERVAL SELECTION IN AN IMPLANTABLE MEDICAL DEVICE

RELATED APPLICATION

This application is a divisional of U.S. patent application Ser. No. 11/257,715, flied Oct. 25, 2005, U.S. Pat. No. 7,769, 449, entitled "SYSTEM AND METHOD OF AV INTERVAL SELECTION IN AN IMPLANTABLE MEDICAL DEVICE", herein incorporated by reference in its entirety.

BACKGROUND

1. Field of the Invention

The present invention relates to implantable medical devices. More specifically, the present invention relates to implantable medical devices that are capable of delivering pacing stimuli.

2. Description of the Related Art

At a superficial level, the mechanical aspects of the cardiac cycle of the human heart are fundamentally simple. The heart has four chambers. Deoxygenated blood is returned from the body to the right atrium. The right atrium (RA) fills the right ventricle (RV), which, upon contraction, pumps blood to the lungs. Oxygenated blood from the lungs fills the left atrium (LA), which in turn fills the left ventricle (LV). The contraction of the left ventricle then delivers oxygenated blood throughout the body. Thus, the atrial chambers serve the purpose of filling their respective ventricular chambers.

Similarly, the electrical and timing aspects of the cardiac cycle are also fundamentally simple, at a superficial level. The sinoatrial node (SA node) is the heart's natural pacemaker and initiates electrical depolarization of the heart at a predetermined rate, based upon physiologic need. The SA node is located in the right atrium and upon activation, the atrial chambers respond to the depolarization by engaging in a muscular contraction. The depolarization wavefront eventually reaches the AV node, where a delay is imparted before depolarizing and contracting the ventricles.

The cardiac cycle is often described by atrial (A) events and ventricular (V) events. Thus, the activation of the SA node is an intrinsic atrial depolarization. Some time later, the ventricles depolarize. There is a delay and the process is repeated. Thus, normal timing is A-V-A-V, etc. For purposes of understanding the physiology as well as for programming various pacemakers, this simple understanding provides several common variables. The rate of the heart is defined by a complete cycle and may either be an A-A interval or V-V interval (A-A will be used herein for explanatory purposes). The time between the atrial event and the ventricular event is the AV interval and not surprisingly, the time between the ventricular event and the subsequent atrial event is the VA interval.

As rate is increased, the A-A interval decreases in duration. The AV node modifies the delay imparted, thus the AV interval is also reduced. The mechanical actions involved (contraction of a chamber; ejection of a fluid) may occur more quickly, but there is a limit or minimal time required for efficacious operation.

This highly simplified overview can actually provide for many of the key programming parameters in a given dual chamber pacemaker. Typically, a dual chamber pacemaker will have an atrial lead (and electrode) positioned within the right atrium and a ventricular lead (and electrode) positioned within the right ventricle, generally with the electrode positioned at the right ventricular apex. Assuming a given patient had no intrinsic rhythm and fully relied upon the pacemaker, the rate would always be the device's escape interval which defines an A-A interval. This interval may be varied by the device based upon sensor input to provide rate responsive (RR) pacing. An AVI or AV interval is programmed and may be varied by the device depending upon rate or other factors. AV synchrony is maintained in that a ventricular paced event (VP) will always follow an atrial paced event (AP). A typical DDD pacemaker may operate in this manner.

While the present discussion is overtly superficial both in terms of the cardiac cycle and operation of a pacemaker, several fundamental aspects have been illustrated that are currently being questioned. The first is that ventricular pacing in the right ventricular apex may not be hemodynamically optimal for all patients. The second is that a programmed AV interval that more or less assures ventricular pacing, even to maintain synchrony, is not necessarily optimal in all patients. Finally, the entirety of the above discussion was in terms of RA to RV electrical timing, which while common parlance tends to ignore a great many aspects of the cardiac cycle.

Implanting leads into the right atrium and right ventricle is significantly easier than implanting leads to pace the left atrium or left ventricle, as leads on the left side are preferably implanted epicardially or within the veins of the heart proximate, but external to the relevant left sided chamber. That is, there is a general medical bias against placing leads or electrodes within the left atrium or left ventricle as this could promote clotting that results in a thrombus. Thus, right side implantation of single or dual chamber pacemakers is the norm. When dual chamber pacemakers are so implanted, the device is typically programmed to operate in a DDD mode or VDD for a single chamber, ventricular pacemaker. Such settings restore rhythm, but ensure that pacing occurs in a high percentage of cardiac cycles.

Ventricular pacing from the right ventricular apex causes the depolarization wave to travel a rather unnatural path and while it will cause the left ventricle to depolarize, the timing of the left ventricle with respect to the right ventricle is skewed electrically and mechanically. Recently, there has been recognition that intrinsic conduction is preferable to pacing in most cases. That is, even if the AV delay is longer than "normal," it is preferable to wait for the intrinsically conducted beat than to pace. This is, of course, at odds with standard DDD (or similar) modes, which will provide a ventricular pace after a predetermined interval (AVI), which is usually short enough that it precludes intrinsic conduction. Certain patients who are pacemaker dependant, e.g., those that have complete heart block, will require and benefit from such ventricular pacing. Other patients may have pacemakers implanted for other reasons and have intact conduction or may have intermittent block. For those patients, intrinsic conduction is often if not always possible and is typically precluded by standard DDD mode settings.

Again referencing a device having leads in the right atrium and/or right ventricle, the timing relied upon both for programming/discussion purposes as well as what is sensed by the implanted device is based upon right side electrical timing. The use of right side timing will tend to ignore the delays in left sided response that occur naturally and/or as the result of pacing. In a normal, healthy heart the SA node will depolarize and generate a wavefront along an atrial conduction pathway that eventually reaches the left atrium causing it to depolarize and contract. The wavefront also reaches the AV node and progresses along the Bundle of His. The left sided pathway propagates somewhat faster than the right, but because the right ventricle is smaller the wavefront leads to a generally synchronized mechanical contraction of both ventricles.

When atrial pacing is introduced, the electrode is typically offset from the SA node, commonly in the right atrial appendage, and different conduction (and possibly less efficient) pathways are taken. See U.S. Pat. No. 5,179,949, issued to Chirife, which is herein incorporated by reference in its entirety. The net result is that there is an interatrial conduction delay (IACD) that is imposed. That is, the left atrium will depolarize and then contract after a longer interval from the pacing pulse than would occur intrinsically, i.e., after the SA node initiates depolarization. Thus, if the remainder of the conduction pathway were intact, this would skew the results for ventricular sensing. That is, an A pace occurs and after some interval, ventricular depolarization is sensed in the right ventricle by the pacemaker. This duration is determined to be the AV interval. However, the left atrium did not depolarize simultaneously with the A pace, nor within the normal physiologic window. Thus, the left sided AV (LAV) interval is shorter than the sensed right sided (RAV) interval. That is, LAV=RAV−IACD.

Another left sided variation to timing occurs when right sided ventricular pacing, particularly at the right ventricular apex is provided. As indicated, normal ventricular conduction begins at the AV node and more or less simultaneously propagates along a left and right side of the Bundle of His and spreads around each ventricle. With right sided pacing, the normal conduction pathway is not necessarily activated and instead propagation from cell to cell may occur at a slower rate. In addition, the wavefront propagates from the apex retrograde along the Bundle of His, then down the left side pathway eventually depolarizing the left ventricle. The delay imparted from the ventricular pace to contraction of the left ventricle is referred to herein as the interventricular conduction delay (IVCD).

Yet another offset is the difference between an event, e.g., an atrial depolarization, and the time at which that event is sensed by the pacemaker. This delay is referred to as the P wave sense offset (PSO).

These various delays are biased towards right side events. That is, failing to account for such delays may have the most consequence on left side activity, which is generally more important to hemodynamic performance.

DETAILED DESCRIPTION

Figure 1:
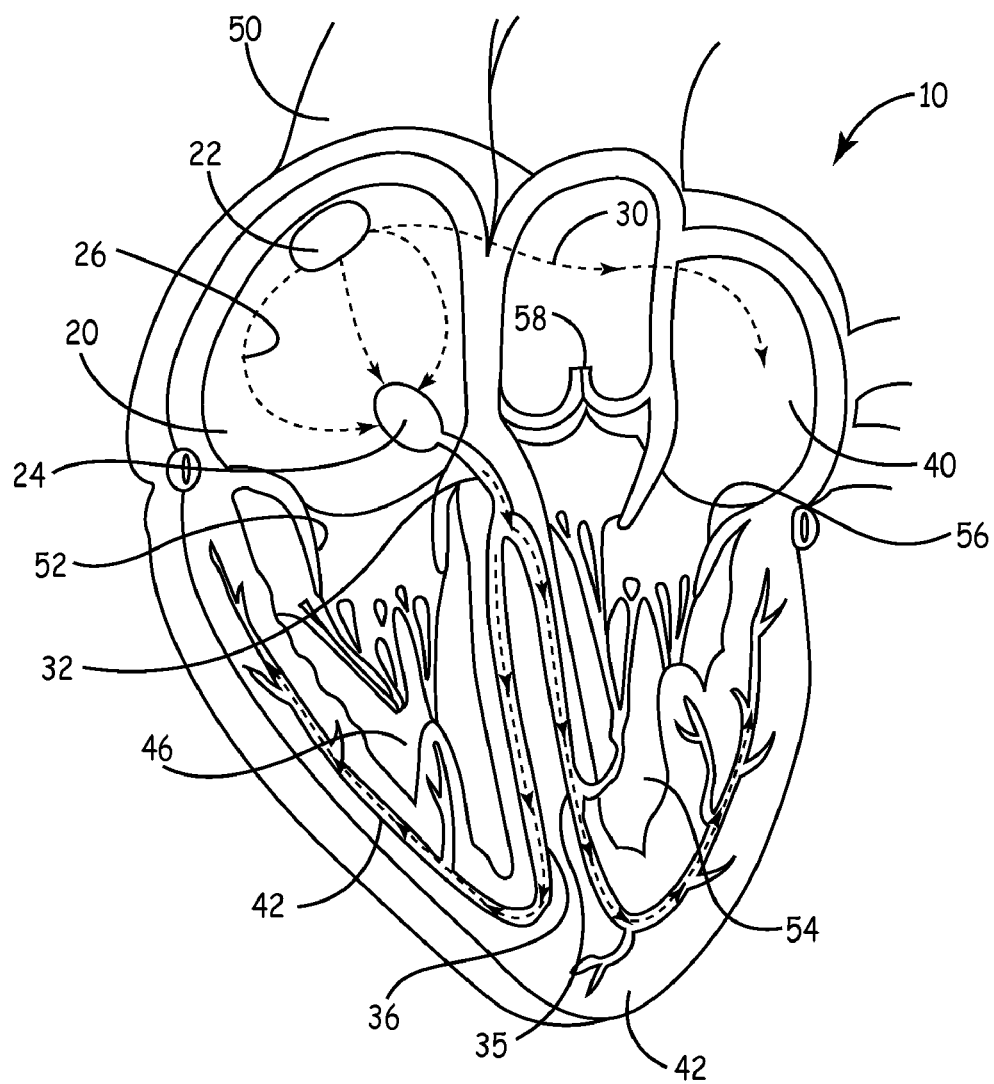
FIG. 1 is schematic, partially sectional view of a human heart.

FIG. 1 is schematic, sectional diagram illustrating the anatomy of a human heart 10. Blood returning from the venous system flows into the right atrium 20 from the superior (SVC) 50 and inferior vena cava. In a normal, healthy heart 10, the sinoatrial (SA) node 22 produces an action potential that is responsible for the automaticity of the cardiac conduction process. A depolarization wavefront is generated and progress through the right atrium (RA) 20 along the atrial conduction pathway 26 to the atrioventricular (AV) node 24. At the same time, the depolarization wavefront propagates from the SA node 22 into the left atrium (LA) 40 along the RA to LA conduction pathway 30. The depolarization wavefront, generally referred to as the P wave triggers a subsequent muscular contraction as it propagates. That is, the electrically detected wavefront, i.e., an EKG, is not identically synchronized with the mechanical contraction.

As blood is filling the RA 20, the LA 40 is similarly being filled via the pulmonary veins. During this time, the right ventricle (RV) 46 and the left ventricle (LV) 54 are being passively filled with blood flowing through the tricuspid valve 52 and the mitral valve 56, respectively. When the atrial chambers mechanically contract, they force an additional volume of blood into the ventricles, causing the ventricles to stretch somewhat. This is referred to as atrial kick and improves overall cardiac output.

When the atrial electrical wavefront reaches the AV node 24, a delay is imparted. This delay provides time for the atrial chambers to contract and fully fill the ventricles, prior to ventricular contraction. After this delay (the PR interval), the depolarization wavefront progresses downward through the ventricular septal wall along the Bundle of His 32 and splits into the left bundle branch (LBB) 35 and right bundle branch (RBB) 36. The bundle branches diverge proximate the apex 42 of the heart 10 and propagate along the Purkinje fibers 41 surrounding the ventricles. Due to the atrial kick, the ventricles are expanded or stretched somewhat. As the muscular contraction occurs in response to depolarization, the fluid pressure within the ventricles increases and causes the tricuspid valve 52 and mitral valve 56 to close. The continued contraction ejects a large percentage of the fluid from the ventricles in a coordinated action. After cardiac cells depolarize, they are refractory for a period of time. The contracted chambers relax and the process repeats.

Figure 2:
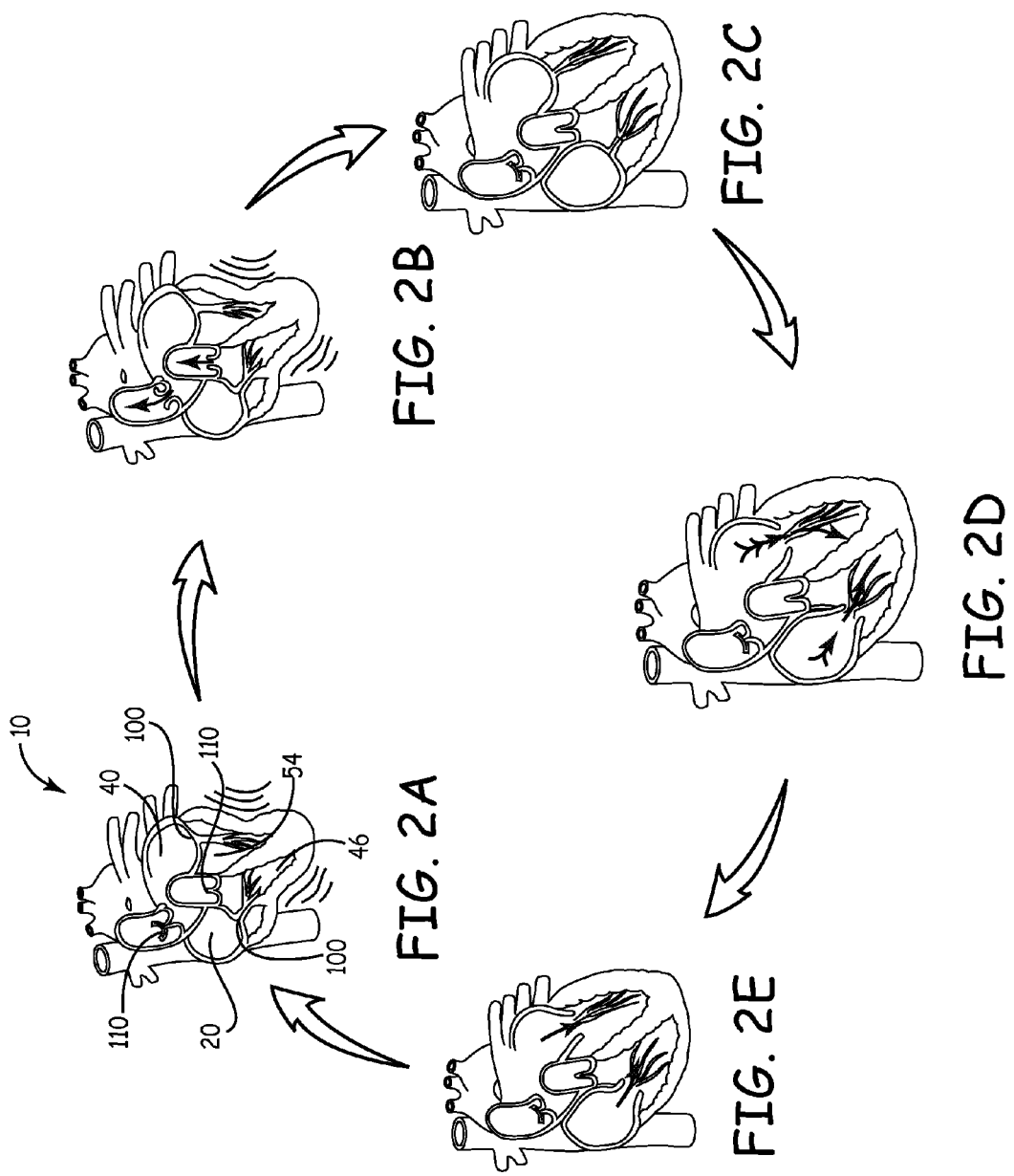
FIGS. 2A-2E illustrate the mechanical contractions of a heart progressing through a cardiac cycle.

FIG. 2 illustrates some of the mechanical and fluid flow characteristics generated during the cardiac cycle. In FIG. 2A, the heart 10 is entering systole and is in the period of isovolumic contraction. The AV valves 100 (mitral and tricuspid) and semilunar valves 110 (aortic and pulmonic) are closed at this point. In FIG. 2B, systole continues with the period of ejection where the outflow of blood opens the semilunar valves 110. FIG. 2C illustrates the onset of diastole and the period of isovolumic relaxation, where all valves (AV and semilunar) are again closed. As diastole continues (FIG. 2D), passive ventricular filling occurs as the pressure within the atrial chambers causes the AV valves 100 to open. During active filling (FIG. 2E), the atrial chambers contract and further fill the ventricles. The process then returns to FIG. 2A and repeats.

Figure 3:
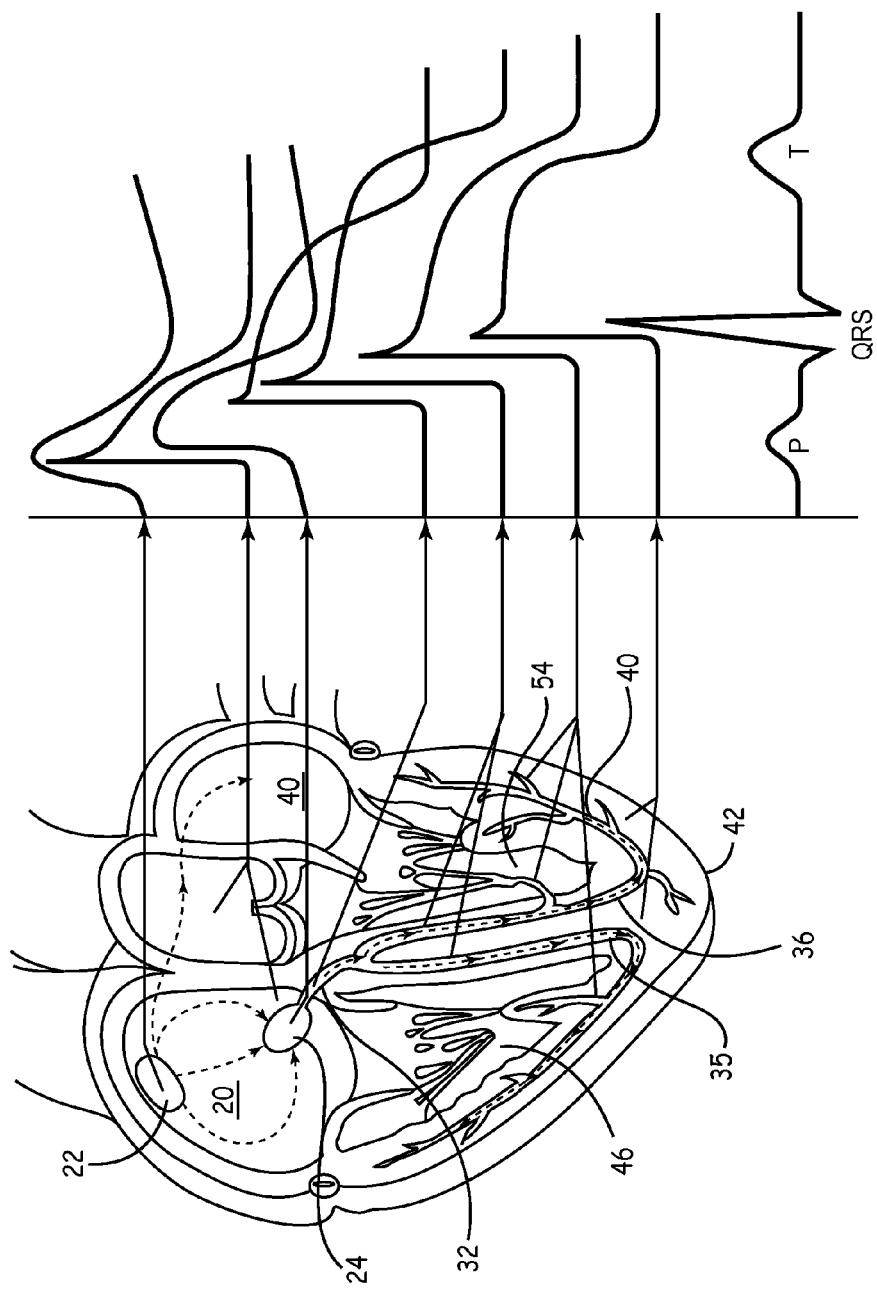
FIG. 3 is illustrates a correspondence between depolarization events occurring throughout a heart and how those events generate a composite EKG tracing.

In describing the cardiac cycle, both electrical and mechanical reference points have been described. Typically, the cardiac cycle is represented electrically and most accurately in that context by a surface EKG. Electrodes on the surface of the skin detect, over multiple vectors, the electrical signals generated as depolarization occurs. A complete cardiac cycle includes a P wave indicative of atrial depolarization, a QRS complex indicative of ventricular depolarization, and a T wave indicative of ventricular repolarization. FIG. 3 illustrates the potential along the conduction pathways and how each portion contributes to the overall represented cycle. Of note, the electrical representation does not indicate any mechanical effect. That is, there is a difference between the onset of electrical activity and mechanical contraction. Likewise, the electrical signals do not represent either the strength of efficacy of a given contraction. Finally, the representative EKG signal is a summation of electrical activity and does not readily allow for differentiation of certain components.

Figure 4:
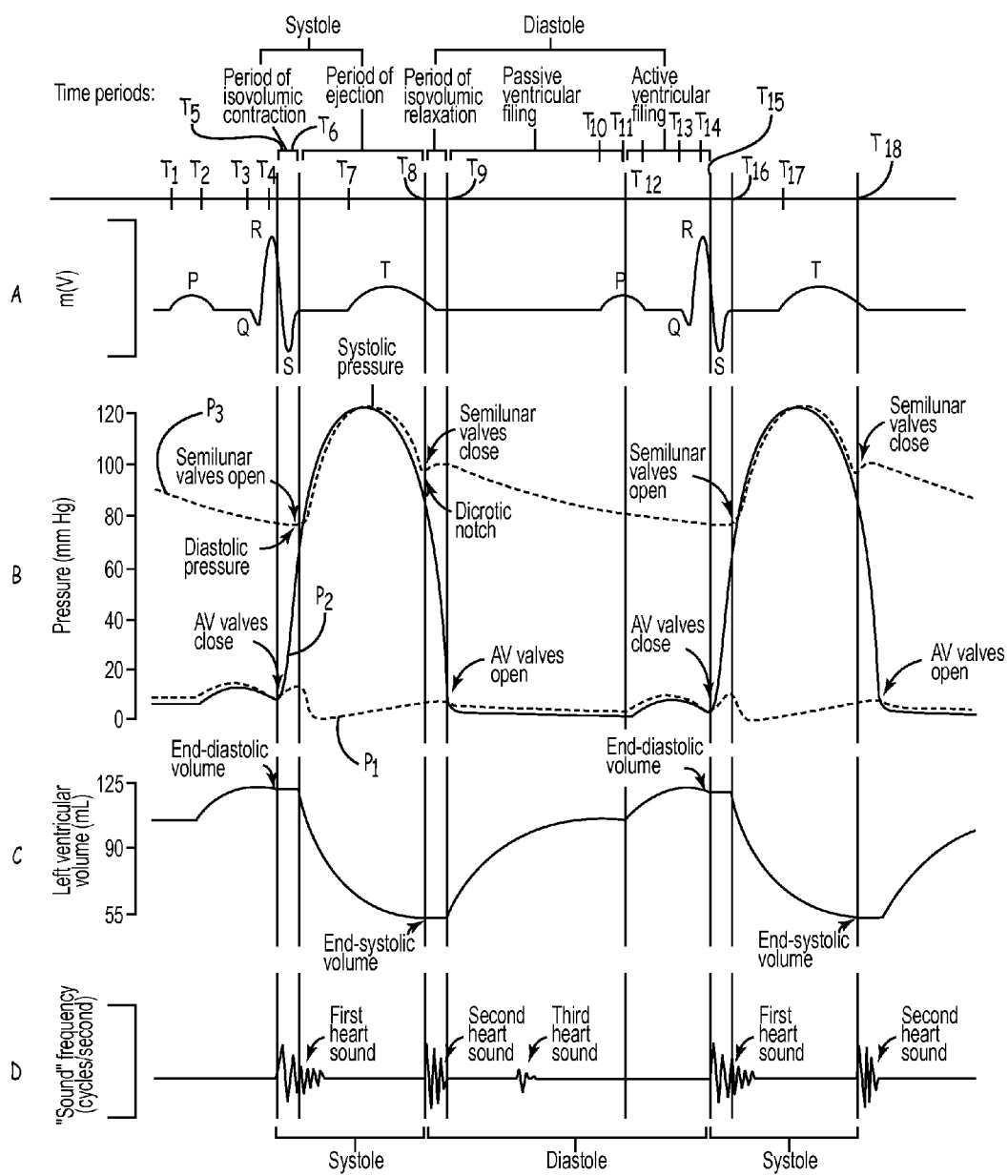
FIG. 4 is a graph illustrating correlations between a surface EKG, pressure data, volume data and heart sounds.

FIG. 4 is a timing diagram that illustrates the correlation in time of an idealized EKG tracing A, pressure graph B, ventricular volume graph C, and heart sound graph D. The pressure graph B includes left atrial pressure P1, left ventricular pressure P2 and aortic pressure P3. At time T1, the surface EKG indicates initiation of the P wave (atrial depolarization); however, there is a delay until LA contraction occurs and begins to increase atrial pressure P1 at time T2. Prior to this point, the LV has been passively filled and with the LA contraction beginning at time T2, a maximum or end diastolic volume is reached at time T5.

Ventricular depolarization begins with the initiation of the QRS complex at time T3. Isovolumic contraction of the LV begins after a delay at time T5 and the pressure within the LV causes the mitral valve to close. Pressure P2 within the LV increases but the semilunar valves remain closed until this pressure exceeds that within the aorta P3 at time T6. When the LV pressure P2 exceeds aortic pressure P3, the semilunar valves open at time T6. LV pressure P2 continues to increase until approximately time T7 and then begins to drop. The period of ejection occurs between time T6 and T8 and LV volume (graph C) falls as blood is ejected from the LV into the arterial system. The T wave, or repolarization, begins during the period of ejection, as illustrated.

When the falling LV pressure P2 is exceeded by aortic pressure P3, the semilunar valves close at time T8. The time period referred to as isovolumic relaxation occurs between times T8 ad T9. During this time, LV pressure P2 is falling rapidly, but is still in excess of LA pressure; thus keeping the mitral valve closed. At time T9, the LV pressure P2 falls below the LA pressure P1 and the mitral valve opens. This begins the period of passive ventricular filling that occurs up until time T11.

A second cardiac cycle is illustrated with the initiation of the P wave at time T10, initiation of active LV filling at T11, start of the QRS complex at time T13, R wave at time T14 and isovolumic contraction from T15-T16. The T wave begins at time T17 and isovolumic relaxation begins at time T18. Thus, one complete cardiac cycle may be defined from a first P wave at time T1 to a second P wave at time T10. Similarly, the cycle may be defined by a first R wave at time T4 to a second R wave at time T14. The surface EKG illustrates the intuition of a P wave at time T1. It should be appreciated that for a variety of reasons, an implanted device might not sense this same P wave at time T1. Rather, the implanted device will sense the P wave at time T1+PSO, where PSO is a P-wave sense offset. Depending upon lead placement and location, sensed activation is not necessarily the earliest actual activation. While this does not change the times at which the other events occur, it does change how the electrical representation or at least a portion thereof would be shifted with respect to the actual occurrence of these other events.

Cycle length (CL), as used herein is simply the length of a given cycle (e.g., T1 to T10) and may vary on a beat to beat basis due to physiologic demand for an intrinsic rate or controlled by a pacemaker based upon programmed parameters and various sensory input. As cycle length decreases, the AV interval (T1 to T3) is able to slightly decrease. Similarly, ventricular diastole may be shortened.

Such variation based upon dynamic cycle lengths is normal within certain parameters. The present invention relates to promoting intrinsic conduction without permitting these variations from exceeding those normal parameters. As illustrated in FIG. 4, ventricular systole occurs from time T5 with isovolumic contraction and ends at time T8, when isovolumic relaxation begins. This is the time period during which the left ventricle is actually contracting. As used herein, the term electromechanical systole (EMS) begins with either the pacing pulse or R wave depending upon the embodiment, and ends when passive left ventricular filling begins at time T9. In other words, EMS includes a time period initiated by the pacing pulse (or sensed R wave), mechanical systole, and the period of isovolumic relaxation. In some embodiments, EMS ends at time T8 or at a time between T8 and T9, as described herein.

Figure 5:
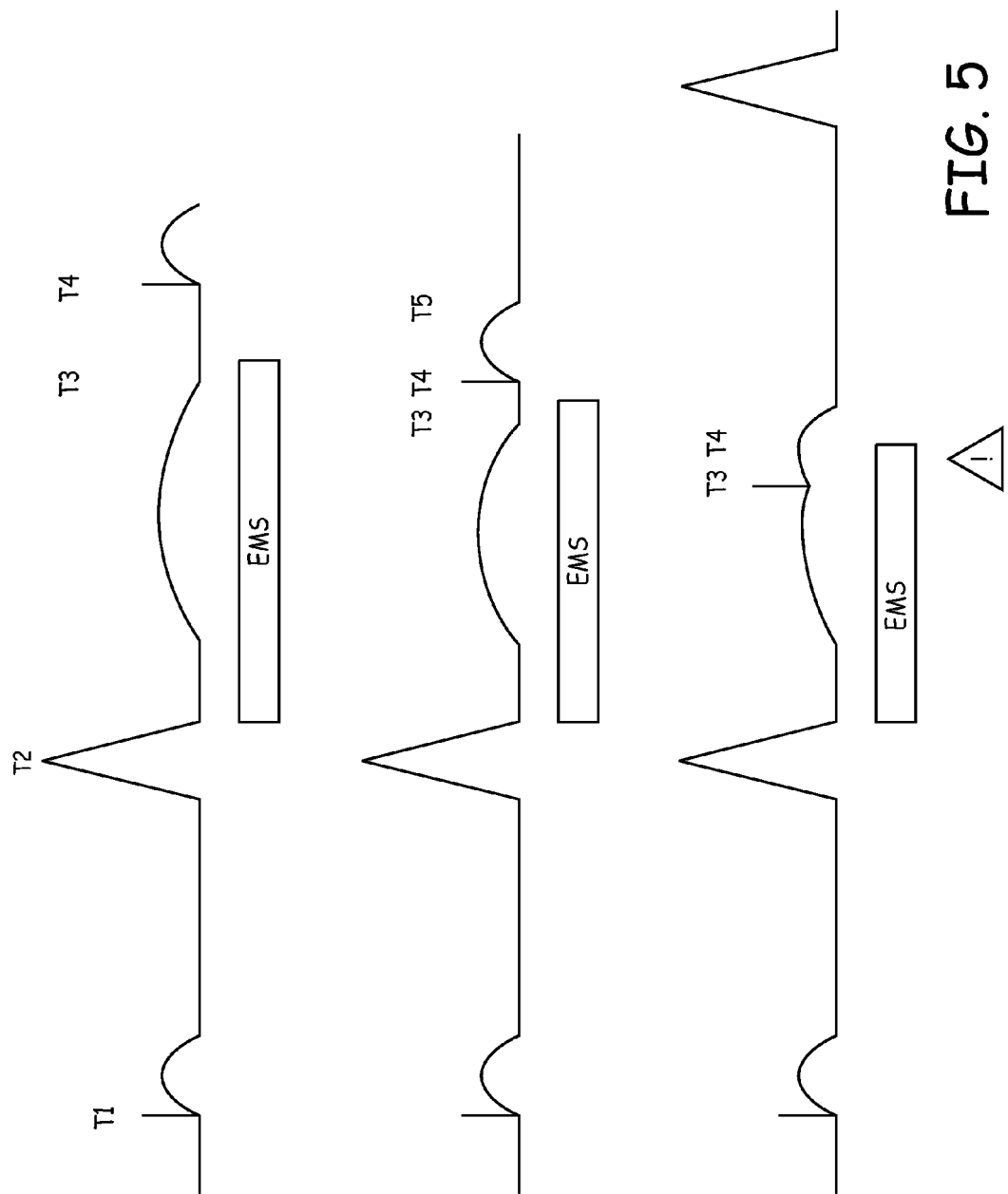
FIG. 5 is a series of stylized EKG tracings.

FIG. 5 illustrates three timing diagrams, schematically illustrating selected events at various times for different heart rates. In each scenario, the AV interval is constant. In scenario A, the heart rate is assumed to be 70 beats per minute (BPM). At time T1, an atrial pace is delivered with an R wave occurring at time T2. The EMS is illustrated through time T3 and a second atrial pace is delivered at time T4. The time difference between T3 and T4 is sufficient for ventricular passive filling (see FIG. 4). In scenario B, the heart rate is 90 BPM; thus, the A-A interval is shorter than in scenario A. Here, the second A pace is delivered at time T4, very close in time to the end of EMS at time T3. This will overlap the period of passive ventricular filling with active filling due to left atrial contraction. Finally, in scenario C, the heart rate is at 110 bpm. As such, the atrial pace is delivered (T3) during the EMS which ends at T4, causing truncation of active atrial flow.

There are two undesired results that may occur as an atrial event encroaches the EMS. The first is that the period for active filling overlaps with passive filling rendering left atrial contraction less efficacious. The second is that atrial contraction occurs (in full or in part) during the EMS. During this time, the ventricular pressure is higher than the atrial pressure. Thus, even with atrial contraction, insufficient pressure is generated to open the AV valves; thus, fluid flow is precluded to the ventricles but does occur retrograde into the pulmonary veins and pulmonary capillary vessels. Mean pulmonary venous pressure will increase and may result in fluid passing from the veins into the pulmonary tissue, impeding normal gas exchange. Symptoms similar to that of heart failure may occur or preexisting pulmonary edema may worsen. The condition may be referred to as pacemaker syndrome or pseudo-pacemaker syndrome if no pacemaker is implanted.

As illustrated, in FIG. 5, this occurs at a higher atrial rate with a constant AV. More accurately, the AV interval (or PR interval) is too long for scenario C; thus leading to the second A pace occurring during the EMS. It should be appreciated, that abnormally long AV intervals may result in the same or similar symptoms even in the absence of atrial pacing.

This situation is commonly averted through the use of a pacemaker operating in a traditional DDD mode. A simple solution is to utilize the standard DDD pacing mode with relatively short AV interval to avoid encroachment; however, as previously mentioned, intrinsic conduction is highly preferable to ventricular pacing when possible. The scenarios illustrated in FIG. 5 indicate atrial pacing and intrinsic R waves. Even assuming that the AV interval is longer than "normal" in all three scenarios, intrinsic R waves occur and at lower heart rates, result in hemodynamically effective cardiac cycles. If a DDD mode were utilized, then a ventricular pace would likely have occurred prior to the intrinsic R wave, precluding the benefits of intrinsic conduction.

On the other end of the spectrum is the use of an AAI pacemaker. In such a case, there is no ventricular sensing or pacing capability; thus, intrinsic conduction is not only fully promoted it is entirely relied upon. In the absence of long AV interval and while conduction is intact, this is a beneficial selection. Of course, with prolonged AV intervals, the encroachment illustrated in FIG. 5 could occur and if heart block occurs, there is no mechanism to provide ventricular pacing.

Thus, the present invention provides a pacing mode that promotes intrinsic conduction to a high degree while providing properly timed ventricular pacing, when required to generally prevent cardiac cycles devoid of ventricular activity. The present invention determines the EMS, which varies based on rate, and calculates a maximum AV interval ($AV_{max}$). The $AV_{max}$ results in an AV interval for any given cycle that allows approximately the longest delay possible to promote intrinsic conduction while still being able to deliver a ventricular pacing pulse, leading to left ventricular contraction that is not encroached upon by a subsequent left atrial contraction.

With reference to FIG. 4, the EMS is a combination of electrical and mechanical events that are not readily identifiable by implanted devices. It should be appreciated that the idealized representation presented in FIG. 4 is not simply reproducible by an implantable device. For example, the EKG illustrated is a surface EKG. Implantable devices generate an electrogram (EGM), which identifies certain electrical activity along selected vectors and in specific sites within the heart. In addition, the PSO will shift the correlation of detected electrical events. Left atrial and left ventricular pressures are not readily measured in general, and certainly not available to a typical dual chamber (right sided) pacemaker. Likewise ventricular volume data is not available to a typical implanted device. To the extent measurements are made for a given patient they are done via imaging techniques such as an echogram in a controlled environment resulting in a limited data set.

Figure 6:
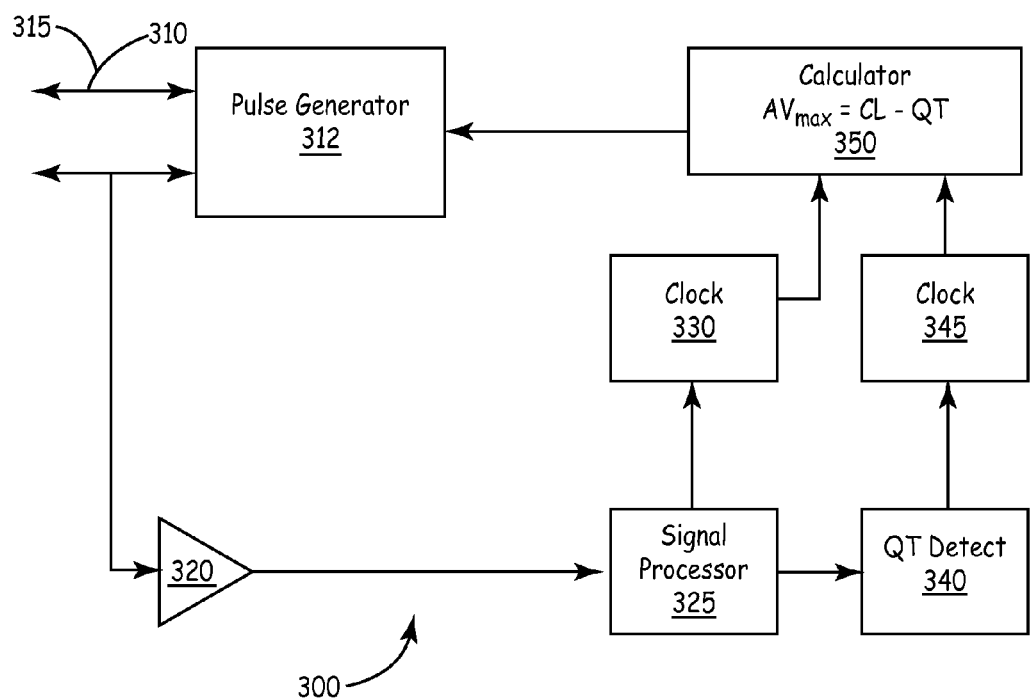
FIG. 6 is a block diagram of a first embodiment of the present invention.

FIG. 6 is a schematic diagram of an implantable pacemaker 300. It should be appreciated that reference to pacemakers would also include implantable cardioverter-defibrillators (ICDs) or similar devices having pacing capabilities. The pacemaker 300 includes various components known in the art and not illustrated herein for clarity, such as a microprocessor, memory, batteries, capacitors, sensors, telemetry components, and the like. An atrial lead 310 and ventricular lead 315 are schematically illustrated as being electrically coupled with a pulse generator 312.

The present embodiment operates in a novel mode having some characteristics similar to DDD/R. VDD/R is another similar mode and it should be appreciated the reference to DDD/R herein would include VDD/R embodiments as appropriate, without further mention. In traditional versions of these modes, an AV interval is set to represent nominal AV delay and provide a long VA (relatively speaking) to avoid the issues described above. As noted, this typically will preclude intrinsic conduction. With the present mode, referred to herein as EMS based DDD/R, the above described EMS is measured, calculated or determined and a maximum AV interval is provided. In this manner, intrinsic conduction is fully promoted for each cycle while avoiding encroachment issues. Furthermore, as left sided effects are more hemodynamically important than right sided effects, the EMS based DDD/R will provide for delays or offsets in left sided timing generated by right sided sensing and/or pacing.

With reference to FIGS. 4 and 6, the timing of the EMS, as described above is approximated by the QT interval. Thus, the pacemaker 300 determines the QT interval by sensing electrical activity through the ventricular lead 315. The sensed data is provided to a QRS amplifier 320 and the output of the amplifier 320 is provided to a signal processor 325. Measurement of the QT interval in and of itself is known and various methods are available. Sensing of the QT interval may involve sensing the intition of the T-wave, initiation of the T-wave with an appropriate offset (similar to the PSO), sensing of a peak amplitude of the T-wave to define a midpoint or median, sensing a point within the second slope of the T-wave (negative normally, positive with inverted T-waves), sensing an endpoint of the T-wave, or calculating/extracting an endpoint of the T-wave using one or more of the above methods. In another embodiment, the patient's QT intervals are clinically measured and an appropriate offset is provided from a point sensed by the device to the determined end of the T-wave. Thus, in subsequent sensing the T wave is sensed and the end of the T wave is calculated.

A signal is provided to a first clock 330, which is responsible for providing a prevailing cycle length CL. This data may be obtained from the ventricular lead 315 by sensing the duration of R-R intervals. Alternatively, other inputs may be provided from an atrial input for A-A intervals or a data location within the pacemaker 300 that indicates the current escape interval. In any event, the first clock 330 represents a means for obtaining a value for a cycle length CL. Ac The signal processor 325 provides data to QT detection module 340, which includes or is in communication with a second clock 345. The QT detection module 340 and clock 345 are responsible for providing a value for the measured or sensed QT interval. The QT interval may begin with a sensed ventricular event or a delivered ventricular pacing pulse. The values for the cycle length CL and QT interval are provided to a calculation module 350 that determines a maximum AV interval, defined as the cycle length minus the QT interval. This $AV_{max}$ value is provided to the pulse generator 312, which sets an AVI (AV interval) equal to the $AV_{max}$ value. Thus, in the next cycle an atrial event (paced or intrinsic) initiates the AVI. This AVI will at least approximate the longest permissible interval to wait for intrinsic conduction without negatively interrupting left atrial transport. It should be appreciated that the duration of the EMS and QT interval are based upon rate, patient specific parameters, inotropic state and other variables. Thus, $AV_{max}$ is calculated on a beat to beat basis.

The $AV_{max}$ is the interval that begins with an atrial event, likely an atrial pacing pulse, and is either terminated by a sensed ventricular event or upon expiration of the interval, a ventricular pacing pulse is delivered. As indicated, this most commonly occurs with a ventricular pacing lead placed within right ventricle. Similarly, the atrial pacing pulse is most commonly delivered via a lead placed in the right atrium. As such, the calculation provided in the calculation module will be $AV_{max}=CL-QT+IAD$ where IAD is the interatrial delay. There are other variables included in the calculation, as discussed below.

Figure 7:
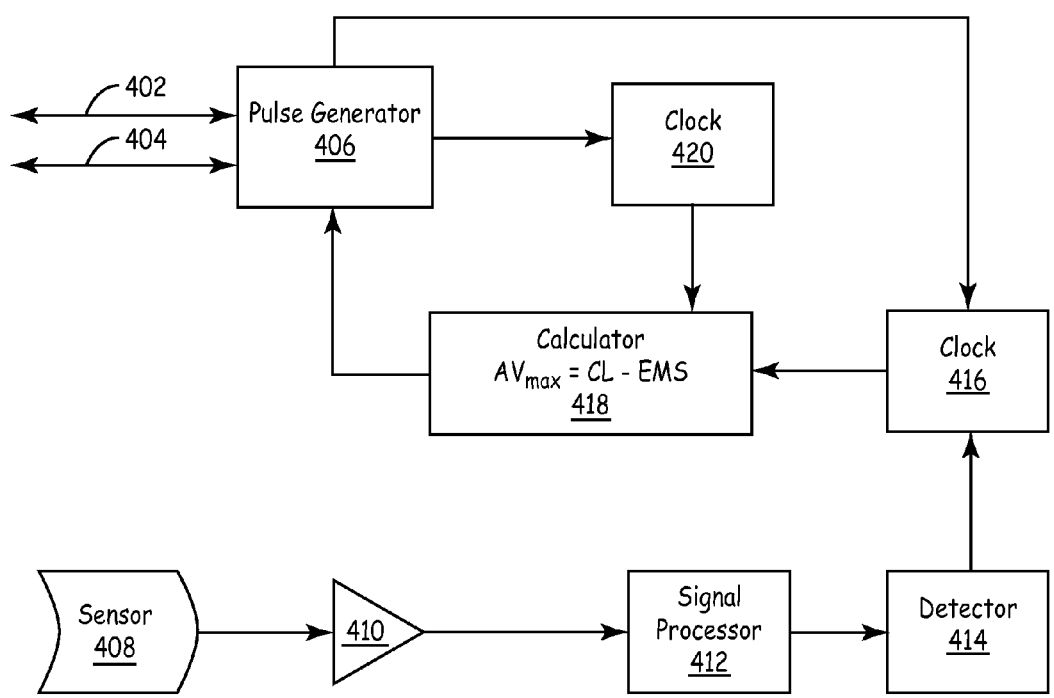
FIG. 7 is a block diagram of a second embodiment of the present invention.

With reference to FIGS. 4 and 7, a second embodiment is shown. A pacemaker 400 includes an atrial lead 402 and a ventricular lead 404 coupled with a pulse generator 406. A sensor 408 is illustrated with an appropriate amplifier 410 and signal processor 412. The output from the signal processor 412 is used in a determination of the end of EMS. The closing of the aortic valve is a physiological marker indicative of the end of EMS. Thus, sensor 408 in one embodiment is a microphone, accelerometer, vibration sensor or similar sensor that detects heart sounds. The closure of the aortic valve causes the second heart sound (S2). Thus, the output of the signal processor 412 is provided to a heart sound detector 414 in communication with clock 416 that triggers the end of the EMS. Again, $AV_{max}=CL-EMS+IAD$ and is calculated in module 418. A second clock 420 is coupled with the pulse generator 406 and module 418. The cycle length is provided to the module either as the escape interval of the pacemaker 400 or sensed rate. The sensed R wave or ventricular pace initiates the clock 416, which terminates upon an indication of the second heart sound. It should be appreciated that the first heart sound (51) is caused primarily by the closure of the AV valves, proximate in time to the QRS complex, the second heart sound (S2) is readily distinguishable as there is a delay of 100-300 ms between the first and second heart sounds.

FIG. 7 illustrates an embodiment that uses one or more sensors to detect heart sounds. The present embodiment alternatively or additionally includes the use of other sensors to identify other physiological markers that indicate the end of EMS. For example, a pressure sensor within the left ventricle or in another anatomical location (e.g., RV) with an appropriate offset, can be used to detect peak negative dP/dt of ventricular pressure. While not exactly correlating to the end of EMS, it could be used as an approximation. Similarly, measuring aortic pressure P3 provides a readily identifiable marker of valve closure, which does correspond to the end of the EMS. Again, direct measurement of these pressure values on the left side is difficult, but if available could be used in the calculation.

Another alternative sensor is an impendence sensor. By generating a sub-threshold electrical signal via one or more pacing leads and/or the can electrode, intracardiac impedance can be measured. U.S. Pat. Nos. 4,719,921 and 5,154,171 relate to impedance measurement and are herein incorporated by reference in their entireties. The end of systole is marked by minimum ventricular volume, which causes the maximum impedance. Thus, impedance measurements may be used to determine EMS. If pressure sensing and/or impedance sensing is utilized, such a sensor would be indicated by sensor 408 in FIG. 7; thus, sensor 408 could be a microphone, vibration sensor, accelerometer, impedance sensor, flow sensor, and/or pressure sensor. While a microphone is illustrated, it should be appreciated that alternative circuitry would be provided to obtain useable signals for other sensor types.

Figure 8:
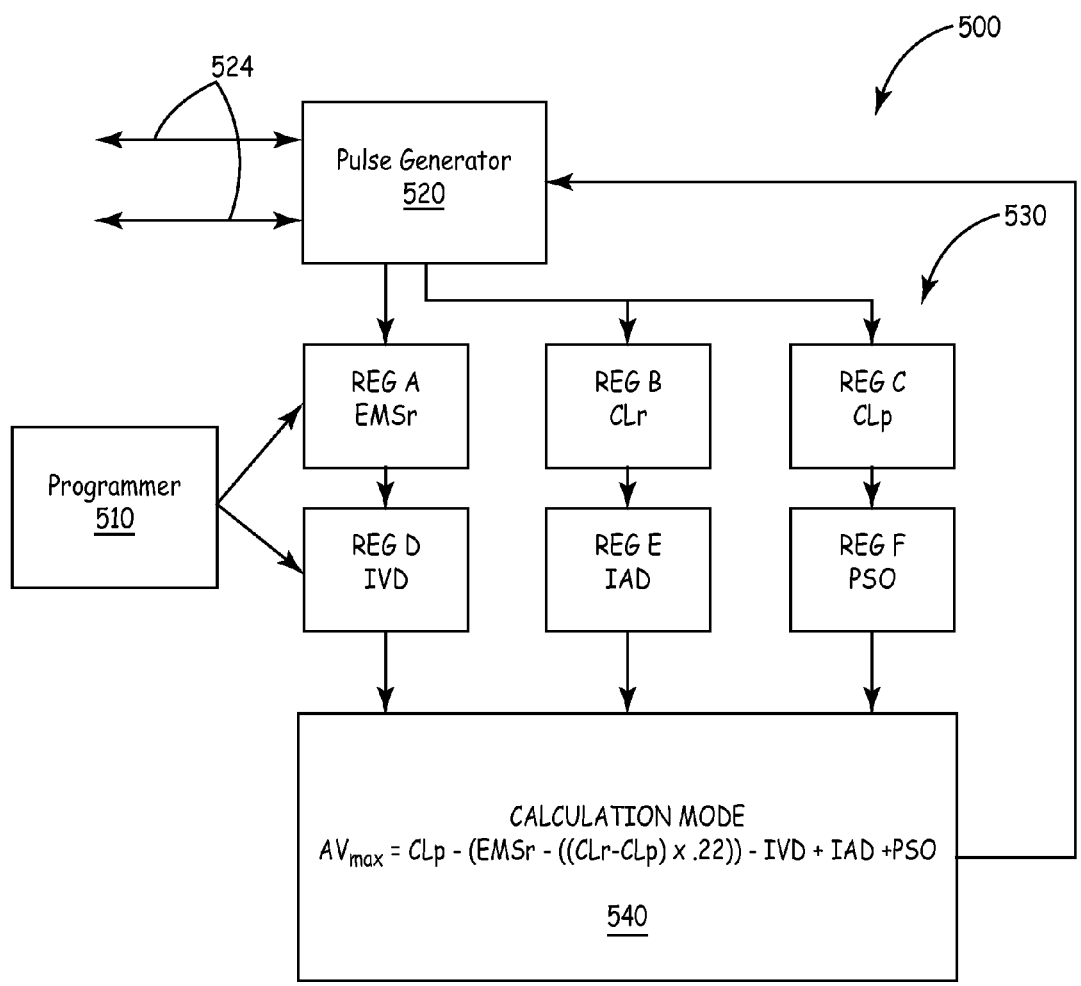
FIG. 8 is a block diagram of a third embodiment of the present invention.

With reference to FIGS. 4 and 8, another embodiment is illustrated. As previously indicated, the EMS parameters are not readily available to current pacemakers or other implantable medical devices. The previous embodiments described herein have provided mechanisms to determine the EMS and then utilize that value in various pacing parameters. The present embodiment provides a mechanism to estimate the EMS on a dynamic and on-going basis without a direct measurement or indicator of the actual EMS. As indicated, the EMS will vary based upon patient specific parameters, interventricular delays, inotropic state, and rate. The pacemaker 500 of FIG. 8 includes a plurality of registers 530 simply representing values that may be stored in memory. The pacemaker 500 is programmed with a medical device programmer 510 via a telemetry system as is known in the art. In summary, at the time of implant or shortly thereafter, clinical observations and measurements are made to provide certain baseline data that is provided to the pacemaker 500. The pacemaker 500 uses this baseline data in combination with sensed or known dynamic data (e.g., cycle length) to determine an appropriate EMS.

A baseline parameter of a resting EMS (EMSr) is made and stored in register A. The resting EMS can be determined in a clinical setting using, for example, Doppler imaging to observe aortic flow, M-mode echocardiography to identify the closure of the aortic valve, catheterization to measure pressure values, QT interval measurement, or phonocardiography to identify the second heart sound. Of course, in a clinical setting there are a number of mechanisms available to make the same or similar observations. By using an EKG or data from the implanted device, the initiation of the EMSr is determined by a sensed R wave, QRS complex, or pacing pulse with the end of the EMSr determined via one of the above measurements. In cases where such measurements cannot be made, nominal values may be utilized based upon generalized clinical observations. A default value for EMSr of about 450 ms may be used for patients having a narrow QRS complex, while a value of 530 ms may be used for patients having left bundle branch block or who require right ventricular pacing.

As indicated, this is a baseline or resting EMSr; thus, the measurements are preferably made while the patient's rate is at a resting rate, which may be the lower rate of the device. Whatever rate is chosen (or occurs) for the resting rate observation, that rate is recorded in register B as the resting cycle length or CLr. Register C is the prevailing or current cycle length CLp. Register D is the interventricular delay IVD that can be measured clinically, Register E is the interatrial conduction delay IACD, having an intrinsic value and an atrial paced value and Register F is the P-wave sense offset.

In use, the prevailing EMS (EMSp) is utilized. The EMSp is dynamic and will change on a beat to beat basis or may be varied at different increments. For example, rate ranges may be utilized where a determined EMSp is utilized so long as the rate remains within that range. In general, the EMS is proportional to cycle length in that a given patient's EMS will decrease as cycle length decreases with about a 1:5 correlation. That is, for every 5 ms that the CL decreases, the EMS will decrease about 1 ms. In one embodiment, a specific correlation of 0.22 is utilized, based upon clinical observation.

Thus, calculation module 540 utilizes the EMSp to determine $AV_{max}$ for a given patient at a particular rate. As indicated, $$AV_{max}=CLp-EMSp-IVD+IAD+PSO$$

$$EMSp=(EMSr-((CLr-CLp)\times 0.22))$$

Using these equations determines the maximum permissible AV interval for a given patient at a given rate that will not interfere with the atrial transport mechanism. The term "maximum" as used herein is meant to indicate approximate or relative values, based upon the efficiencies and capabilities of a given embodiment and is not meant to reference an absolute theoretical or actual maximum specific value.

Figure 9:
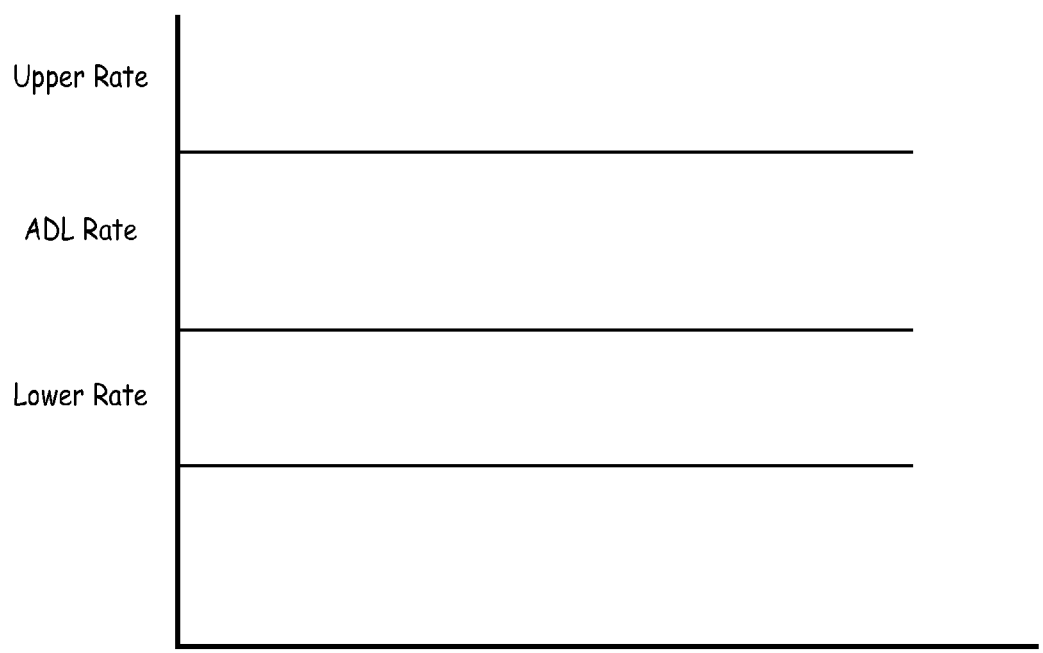
FIG. 9 is a graph illustrating device rate limits.

FIG. 9 is a graph that illustrates certain programmable values for a given pacemaker. As is known, a pacemaker will have a lower rate and an upper rate. The lower rate is the longest permissible cardiac cycle length (e.g., A-A interval) that the pacemaker will permit. Conversely, the upper rate is the fastest rate at which the pacemaker will pace. The values set for these parameters depend upon patient specific parameters. For example, a young, otherwise healthy patient may be expected to exercise vigorously and attain a relatively high heart rate, as opposed to an older, sedentary patient who has little physical activity. The lower rate is the rate applied during period of non-exertion or relaxation. Some pacemakers will have an even lower rate setting (not shown) that is used for when the patient is asleep.

The present invention introduces the programmable activities of daily living (ADL) rate. The area between the Lower Rate and the ADL Rate include rates appropriate for complete rest or inactivity through normally mild physical exertion. For example, a Lower Heart Rate may be 60 bpm. Walking, climbing stairs, household chores and similar activities will typically raise the heart rate, but typically not to a level consistent with prolonged strenuous work or exercise. The programmed value for the ADL will, of course, be patient specific, but as an example a Lower Rate might be 60 bpm, an Upper Rate might be 170 bpm and an ADL Rate may be 90 bpm. In this example, it is presumed that the patient will perform normal daily activities with a heart rate at or below 90 bpm.

As previously discussed, there is a recognition that intrinsically conducted ventricular beats are generally preferable to providing right sided ventricular pacing, even if the intrinsic AV is somewhat prolonged. The above-described embodiments determine a maximum AV interval that can be permitted in any given cardiac cycle. That is, the longest period of time that the device can wait for intrinsic conduction before delivering a ventricular pacing pulse. If a ventricular pacing pulse is delivered after this time or an intrinsic event occurs after this time, the ensuing atrial pace (or atrial event) may occur during EMS and atrial transport block may occur.

This dynamic imposes a binary decision on a per cycle basis. That is, each cardiac cycle is divided into two windows; the first is the $AV_{max}$, during which ventricular activity is permitted and the EMS window (as opposed to the actual EMS which implies ventricular depolarization/contraction). The present invention recognizes four categories that are referred to with respect to the atrial event for a given cycle. The four categories are defined as contributory P-waves, deleterious P-waves, wasted P-waves and sacrificed P-waves.

Figure 10:
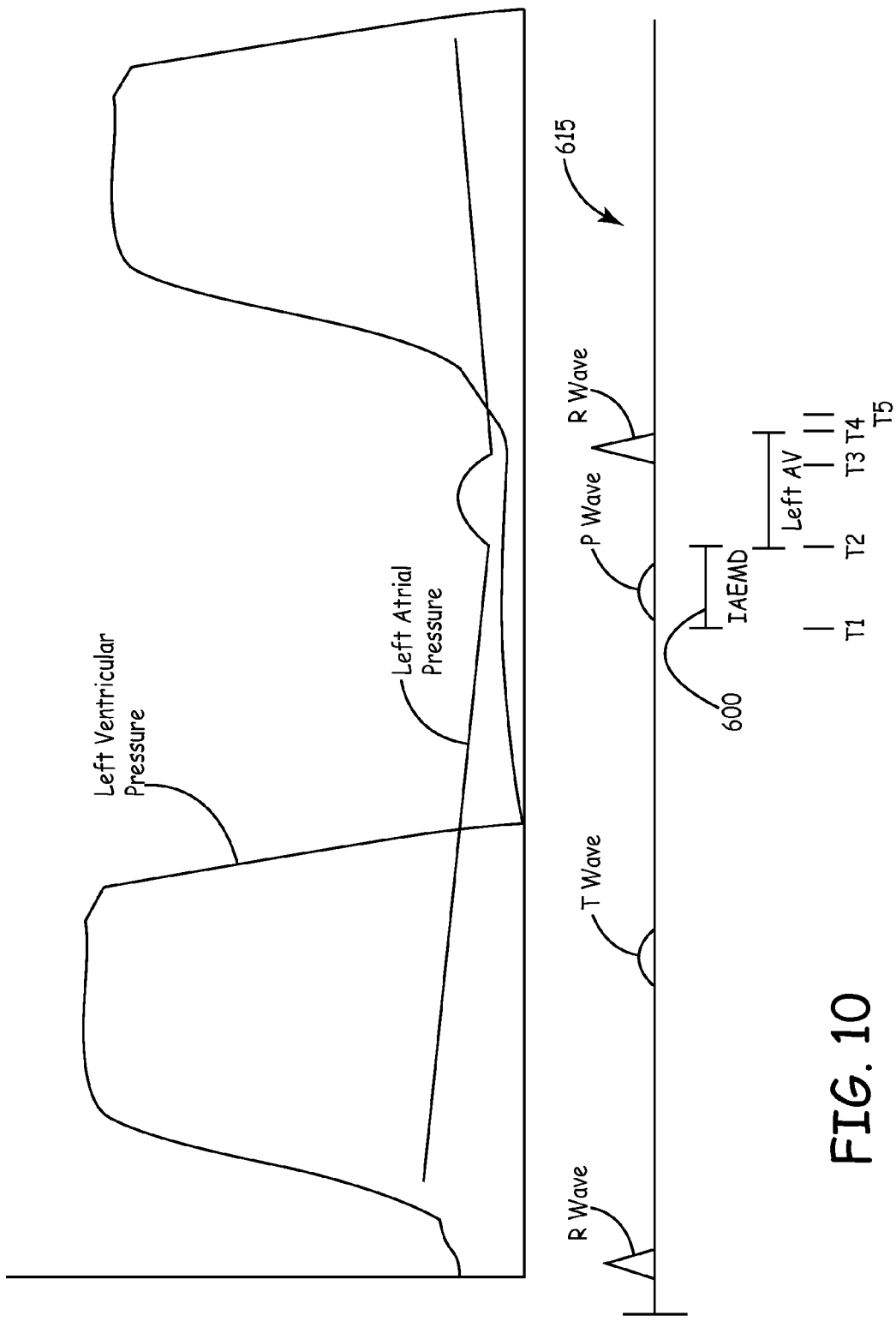
FIGS. 10-13 illustrate stylized pressure waveforms and corresponding EKG data.

FIG. 10 is graph illustrating a stylized EKG tracing 615 synchronized with stylized left atrial pressure LAP and left ventricular pressure LVP tracings. FIG. 10 illustrates a contributory P-wave. At time T1, the EKG indicates atrial depolarization. At time T2, left atrial pressure, as indicted by the LAP tracing, begins to increase. Thus, the interval between T1 and T2 is the IAEMD 600. At time T3, the QRS complex beings and left ventricular pressure begins to rise at time T4. The interval between T2 and T4 is the left sided AV interval (initial left atrial pressure increase to initial left ventricular pressure increase). As indicated in FIG. 10 and in the stylized tracings of FIG. 4, this is ideal timing. After a sufficient period of time for passive filling, the left atrium is able to fully contract and just after this contraction, the left ventricle begins to contract. A contributory P-wave is always desirable.

Figure 11:
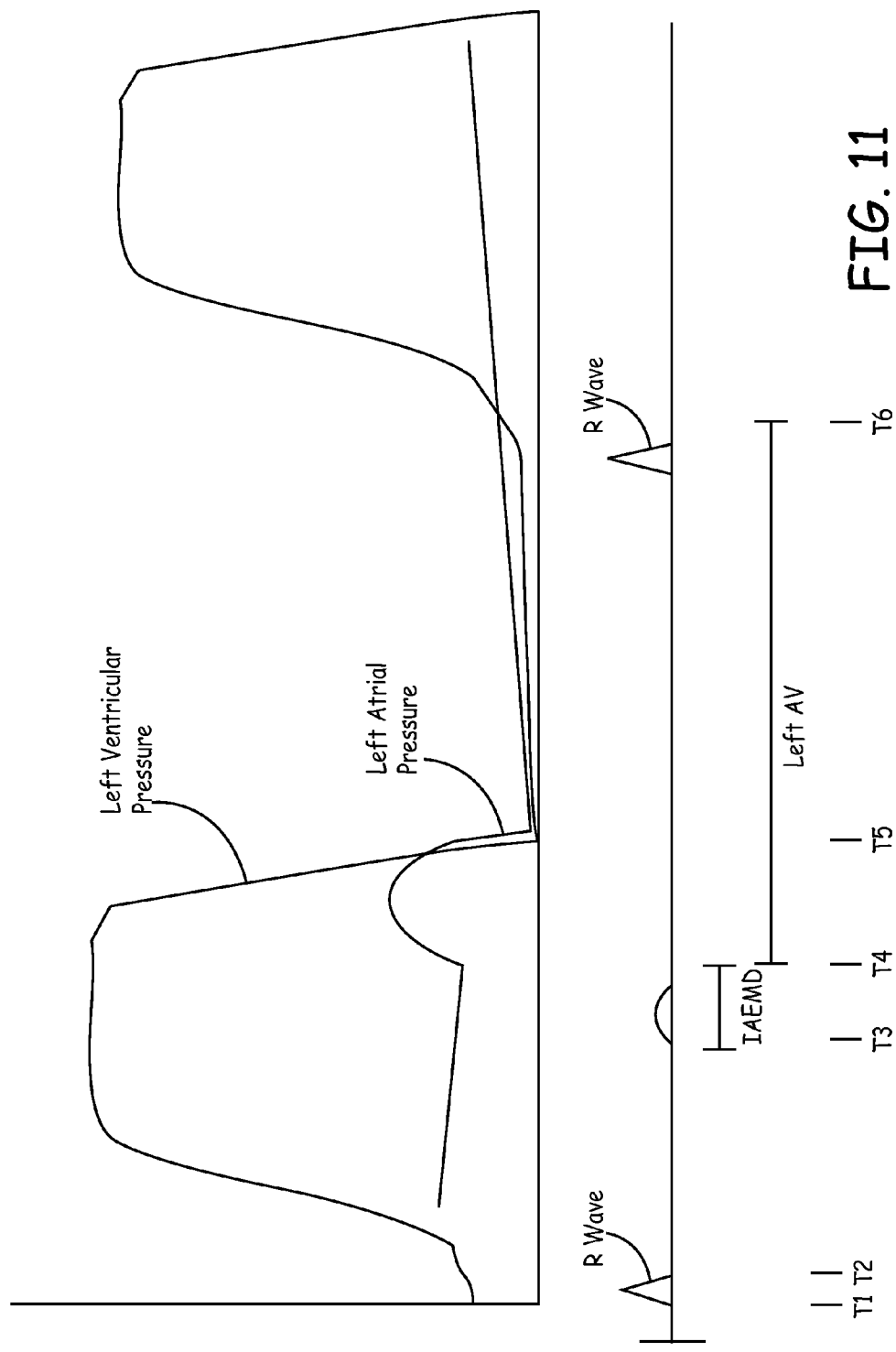

FIG. 11 represents a deleterious P-wave. The same intervals are represented by the same reference numerals; however, the timing is different. At time T1 (approximately), the QRS complex begins. At time T2, left ventricular pressure begins to rise. During left ventricular systole, the P wave is sensed at time T3 and left ventricular pressure begins to rise at time T4. The left ventricle enters diastole at approximately time T5. Thus, almost the entirety of the mechanical atrial contraction occurred during ventricular systole. Thus, the left atrium was not able to deliver blood into the left ventricle during the contraction, resulting in fluid backup into the pulmonary system. This leads to increased stress on the atrium and increased pressure. Deleterious P-waves can vary from the illustrated example, but in general left atrial contraction occurs during or just after ventricular activation such that the atrial contraction contributes little or nothing to ventricular filling. Deleterious P-waves are undesirable and the above embodiments are provided to preclude or greatly reduce their occurrence.

Figure 12:
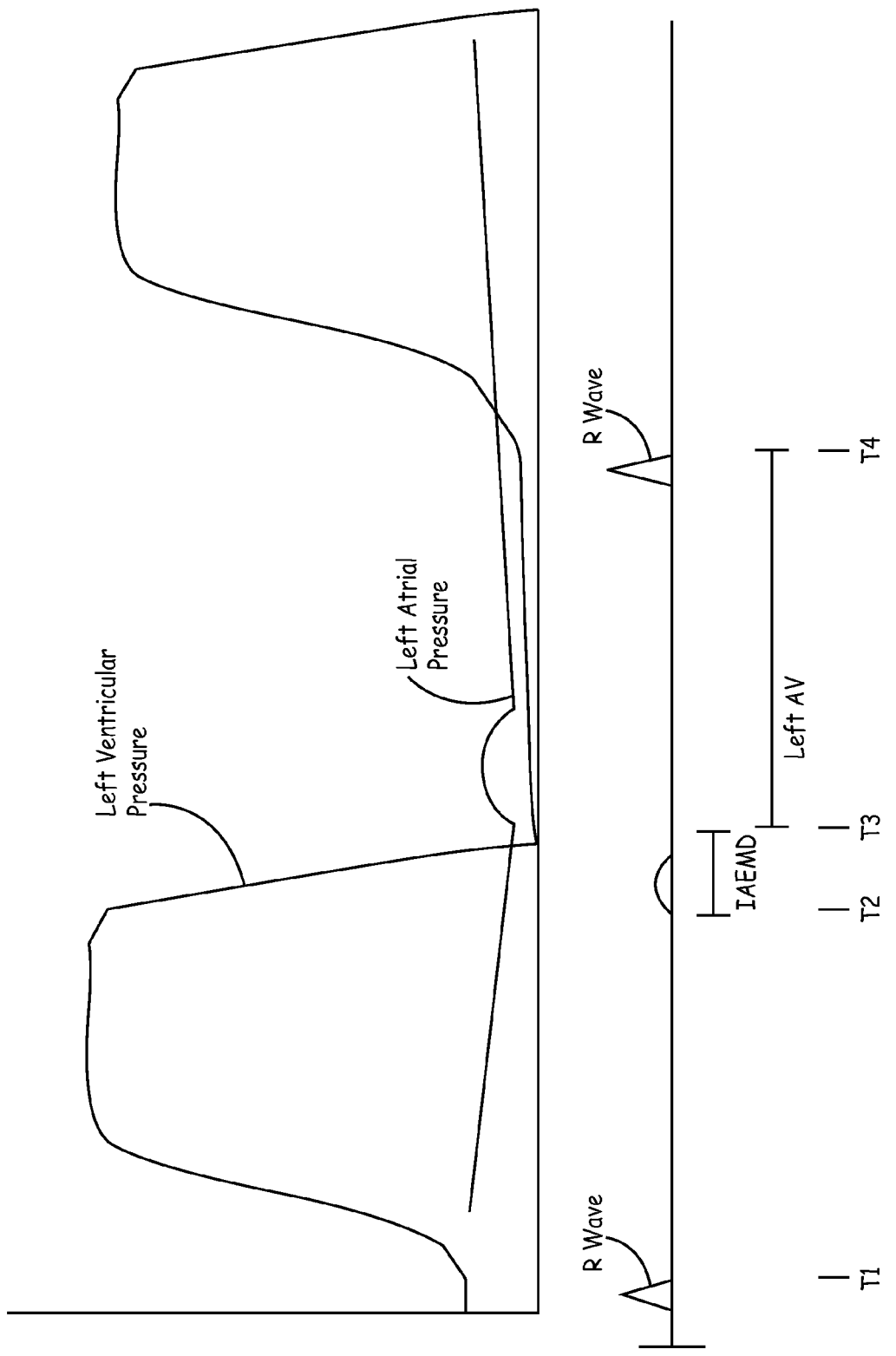

FIG. 12 illustrates what is referred to as a wasted P-wave. Here, the left atrial contraction occurs too early in ventricular diastole to provide meaningful atrial transport and in general, does not contribute to increased cardiac output. At time T1, left ventricular pressure begins to rise. At time T2, the P wave occurs and left atrial contraction begins at time T3. By time T3, the left ventricle has entered diastole, thus the left atrium is not contracting against a closed mitral valve and as such, does not generate pulmonary back flow. However, there has been little or as in this example, no time provided for passive filling and no "atrial kick" is provided, thus the P wave is considered wasted. Intrinsic conduction is however, facilitated.

Figure 13:
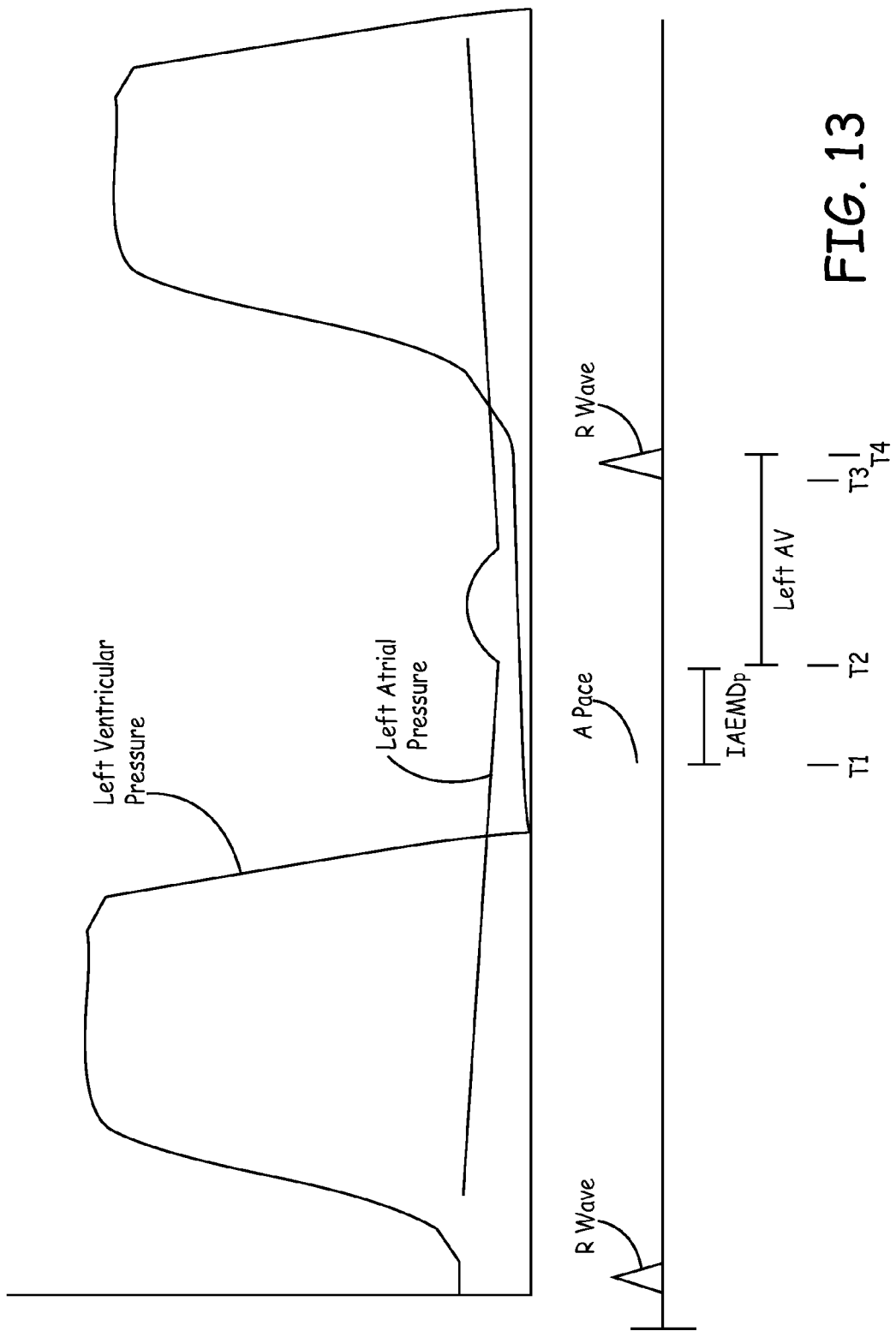

FIG. 13 illustrates a sacrificed P-wave. At time T1, an A pace is delivered and at time T2, left atrial pressure begins to rise. In this example, the left ventricle entered diastole some time prior to T1, so some passive filling has occurred. The sensed QRS complex (intrinsic) occurs at time T3 and left ventricular pressure begins to rise at time T4. Here, the atrial contraction is still too early in diastole to provide meaningful atrial transport; however, intrinsic conduction is facilitated.

Figure 14:
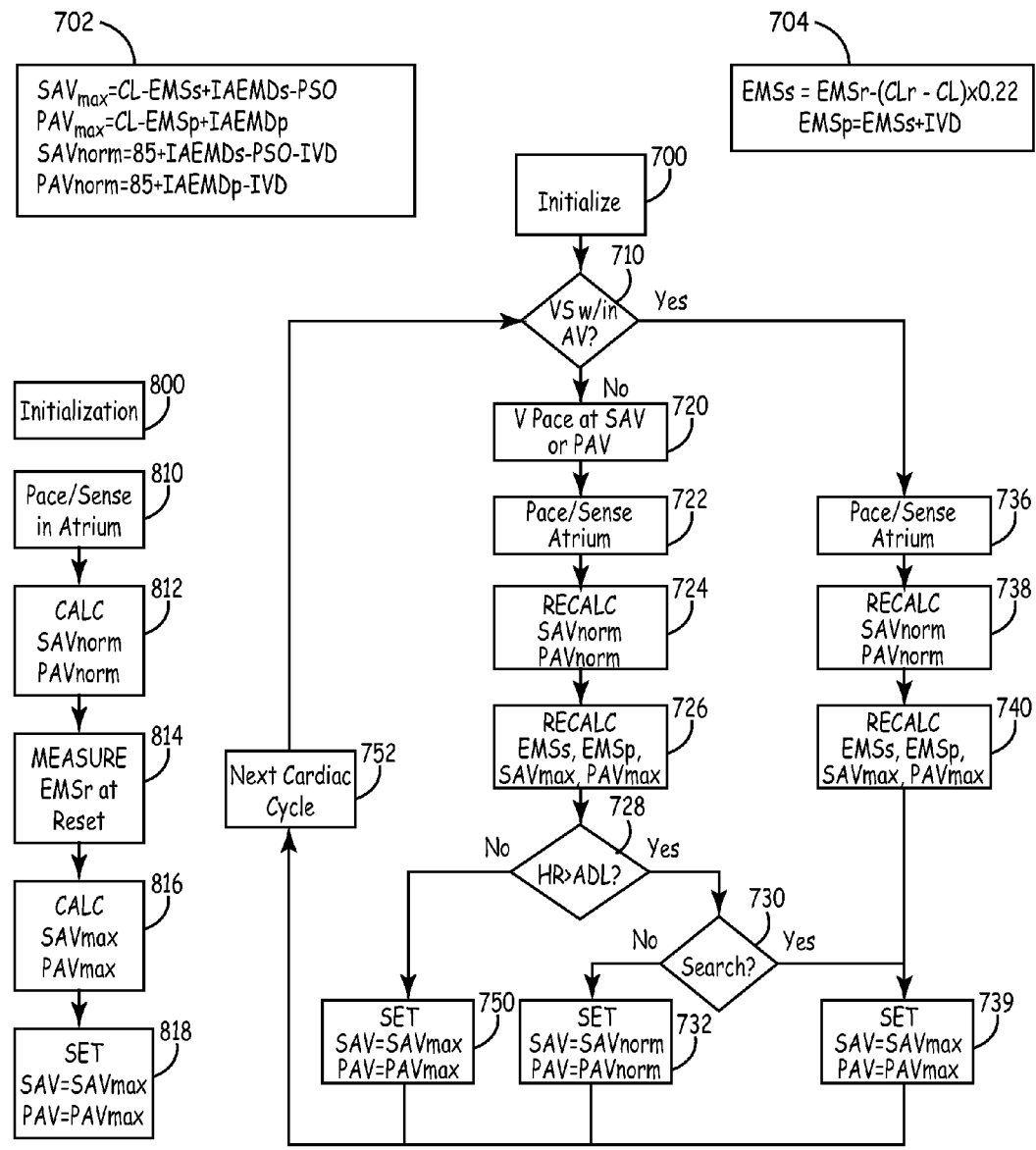
FIGS. 14-16 are flowcharts illustrating processes utilizing embodiments consistent with the teachings of the present invention.

In another aspect of the present invention, the above described embodiments are further modified to promote contributory P-waves, avoid deleterious P waves, and to permit sacrificed P-waves when the patient's heart rate is at or below the ADL rate. In this manner, intrinsic conduction is always promoted to the $AV_{max}$ when at or below the ADL Rate, but above the ADL Rate, efficacious or contributory P-waves are promoted. Even while above the ADL Rate, the AV interval may be longer than that of standard DDD/R or VDD/R pacing to promote intrinsic conduction, FIG. 14 is a flowchart illustrating a process for using an algorithmic based, prevailing EMS to promote intrinsic conduction. The process begins by initializing (700) the sensed AV (SAV) interval and paced AV (PAV) interval values for the implantable medical device (IMD). It should be appreciated that the implanted device may make some or all of the calculations or an external medical device programmer may make some or all of the calculations and provide data to the IMD. The initialization subroutine (800) begins by pacing and/or sensing (810) events in the atrium. During this time, the pacemaker will operate to provide standard therapy, unless modified to obtain specific data. During this initialization process, the device calculates (812) values for $SAV_{norm}$ and $PAV_{norm}$, which indicate the values that will fully promote contributory P-waves. The formulas for the various calculations are indicated in box (702). Specifically, $SAV_{norm}$=85 ms+IAEMDs−PSO−IVD, where IAEMDs is the interatrial electromechanical delay for physiologic or intrinsic atrial depolarizations, PSO is the P-wave sense offset and IVD is the interventricular conduction delay (also referred to as the IVCD). When an intrinsic ventricular event with narrow QRS is sensed, as opposed to pacing the ventricle, the IVD equals zero (0). $PAV_{norm}$=85 ms+IAEMDp−IVD, where IEAMDp is the interatrial electromechanical delay when atrial pacing occurs. It should be appreciated that these variables may be measured for a specific patient or nominal values may be used if measurements are unavailable. The 85 ms is the mean normal value of the mechanical left heart AV interval resulting from clinical studies. It is merely an example and not meant to be limiting, since the normal range extends from 60 to 110 ms in one embodiment 65-105 ms in another. The patient's resting EMS (EMSr) is measured (814) in a manner previously discussed. This value is then used to calculate (816) the $SAV_{max}$ and $PAV_{max}$. The $SAV_{max}$=CL−EMSs+IAEMDs−PSO. The EMSs means the EMS used in a R-sensing situation and equals EMSr−((CLr−CL)×0.22) where CLr is the cycle length occurring when the EMSr was determined and CL is the current or prevailing cycle length. The $PAV_{max}$=CL−EMSp+IAEMDp, where EMSp=EMSs+IVD. The difference is that when ventricular pacing is provided (EMSp), the interventricular conduction delay (IVD) needs to be considered. The initialization process ends by setting the SAV and PAV of the device to the determined $SAV_{max}$ and $PAV_{max}$.

Now the process is described with the device having been initialized. An atrial event will occur to begin a cardiac cycle and is either a sensed event or an atrial pace. The nature of the event determines whether the PAV or SAV interval is used in a given cardiac cycle. During the SAV or PAV, the device senses the ventricles to determine (710) if intrinsic conduction occurs. Assuming the SAV or PAV expires without a ventricular sense, then a ventricular pacing pulse is delivered (720). The device then senses for intrinsic atrial depolarization or provides an atrial pace at the end of the escape interval (722). Though indicated as a subsequent step(s), it should be appreciated that the following calculations may be performed on a beat to beat basis and do not necessarily occur after the atrial event (722). In steps (724) and (726) all of the variables determined during initialization (800) are recalculated with the exception of the EMSr, which is fixed. The EMSs and EMSp values used in the $SAV_{max}$ and $PAV_{max}$ are recalculated.

The device determines (728) if the current heart rate is greater than the programmed ADL rate. If the current heart rate is at or below the ADL rate, then the device continues to employ $SAV_{max}$ and $PAV_{max}$ values. As indicated, these provide the longest period during any given cardiac cycle for intrinsic conduction to occur without interfering with atrial transport, though sacrificial P-waves could occur. The device then progresses (752) into the next cardiac cycle and the process is repeated from step (710).

Returning to step (728), if the current heart rate exceeds the ADL rate, the device determines (730) whether a search for intrinsic conduction should occur. This search will be described shortly; however, assuming it is not an appropriate time for a search or this is the first interval with the heart rate exceeding the ADL rate, the device sets (732) the values for SAV and PAV to $SAV_{norm}$ and $PAV_{norm}$ respectively.

As previously indicated, these are shorter AV intervals (as compared to max values), so intrinsic conduction is given less chance while a delivered ventricular pace is more optimally timed. In other words, following the flow of this logic diagram, to get to this point this cardiac cycle has received a ventricular pace. The previous cycles may have likewise been paced; thus, there is at least an increased likelihood that the next cardiac cycle will have a ventricular pace. As such, if there is to be a ventricular pace and the heart rate is above the ADL, then setting the SAV and PAV to $SAV_{norm}$ and $PAV_{norm}$ respectively causes the delivered pacing pulse to occur after a normalized AV interval, rather than a maximized AV interval. It should be appreciated, that this feature can be disabled through the medical device programmer, in some embodiments. Thus, the physician may choose to utilize $SAV_{max}$ and $PAV_{max}$ regardless of heart rate.

If at step (728), the current heart rate is at or below the ADL, then the SAV and PAV are set to $SAV_{max}$ and $PAV_{max}$ as the promotion of intrinsic conduction takes precedence. The next cardiac cycle begins (752) and the process repeats.

When the ADL is greater than the current heart rated at step (728), the next step is to determine if a search should be performed (730). As indicated, if this is negative, then the values are set to the "norm" values in step (732). If the device determines that it is time to perform a search, then the SAV and PAV are set to $SAV_{max}$ and $PAV_{max}$ (739) and the next cardiac cycle (752) proceeds with these longer AV intervals. This provides an opportunity to return to intrinsic conduction, if for example, transient heart block had occurred but was now terminated.

The search (730) is conducted at periodic intervals. In one embodiment, a search is performed in the cardiac cycle immediately subsequent to the first cycle that has a ventricular pace. Then, assuming ventricular pacing is occurring with each iteration of step (720), the searches are performed after progressively longer intervals. For example, after 30 seconds, after one minute, after 2 minutes, then 4, 8, 12, 24 minutes, etc. Unless the ADL is set inappropriately for a given patient, they are unlikely to sustain heart rates above the ADL for excessively long periods of time. Thus, if the heart rate is above the ADL for what the physician may choose as an excessive period of time, this data may be reported as a potential error or indicator of a physiologic concern. Perhaps a young, very active person may have a physically demanding job where their heart is elevated for longer periods of time. Such data may simply be noted or the ADL may be raised for this patient. Conversely, if a patient who has very limited physical capabilities is above the ADL for a prolonged period of time, this may indicate a concern. It should be appreciated that the present device and the present algorithms are not meant to address tachyarrhythmias. It should be understood, however, that the device may very well have algorithms to address and/or provide therapy for tachyarrhythmias and this is separate from the evaluation occurring at step (728). That is, if the device detects a tachyarrhythmia, the therapy may involve departing from the present algorithm and providing anti-tachy pacing, defibrillation or other therapies.

If a ventricular event is sensed during the AV for that cycle (710), the process proceeds to step (736). Steps (736), (738) and (740) are the same as steps (722), (724), and (726) respectively. Subsequent to step (740), the device sets the SAV and PAV to $SAV_{max}$ and $PAV_{max}$, respectively. Absent ventricular pacing, this is not a change other than the intervals for those variables are recalculated with each cycle (740). Alternatively, if during a previous cycle ventricular pacing had occurred and the SAV and PAV were set to $SAV_{norm}$ and $PAV_{norm}$ (732), the step (734) represents a change to $SAV_{max}$ and $PAV_{max}$.

To summarize, once the device sets the SAV and PAV to $SAV_{norm}$ and $PAV_{norm}$, there are three ways in which the algorithm will return to $SAV_{max}$ and $PAV_{max}$. The first is that the heart rate is at or below the ADL (728). The second is that a search (730) for conduction is performed. The third is that a ventricular event is sensed during the $SAV_{norm}$ or $PAV_{norm}$ interval. Conversely, in this embodiment, the only time the $SAV_{norm}$ or $PAV_{norm}$ values are utilized is when the heart rate is above the ADL, a ventricular pace has occurred in the present cycle and a search is not being performed.

In the illustrated embodiment, the SAV and PAV values will not be set to "norm" values if there is a sensed ventricular event. This assumes that intrinsic conduction, even if occurring in the interval between $AV_{norm}$ and $AV_{max}$, is preferable to right ventricular pacing. In an alternative embodiment not separately illustrated, the AV intervals are set to "norm" values whenever the heart rate exceeds the ADL Rate, whether or not the ventricular event was sensed or paced. In such an embodiment, the search (730) is rendered moot and may be eliminated. This may be an option provided to caregivers and/or patients. For example, some caregivers or patients may believe that during periods of exercise (heart rate above ADL), they feel or perform better with ventricular pacing. Thus, the clinician may have the option of selecting or disabling this parameter and/or permitting the patient to selectively enable or disable this parameter. As an example, a given patient may routinely run for exercise. Intrinsic conduction may be preferable at most times, even when the heart rate exceeds the ADL rate for other reasons; however, while running the patient may enable the "norm" values. This may be accomplished with a patient activator in telemetric communication with the device or by other communication means. As another optional feature, the device may revert to the illustrated embodiment after the expiration of some predetermined period of time (e.g., 1 hour, 4 hours, etc.) after patient selection.

Figure 15:
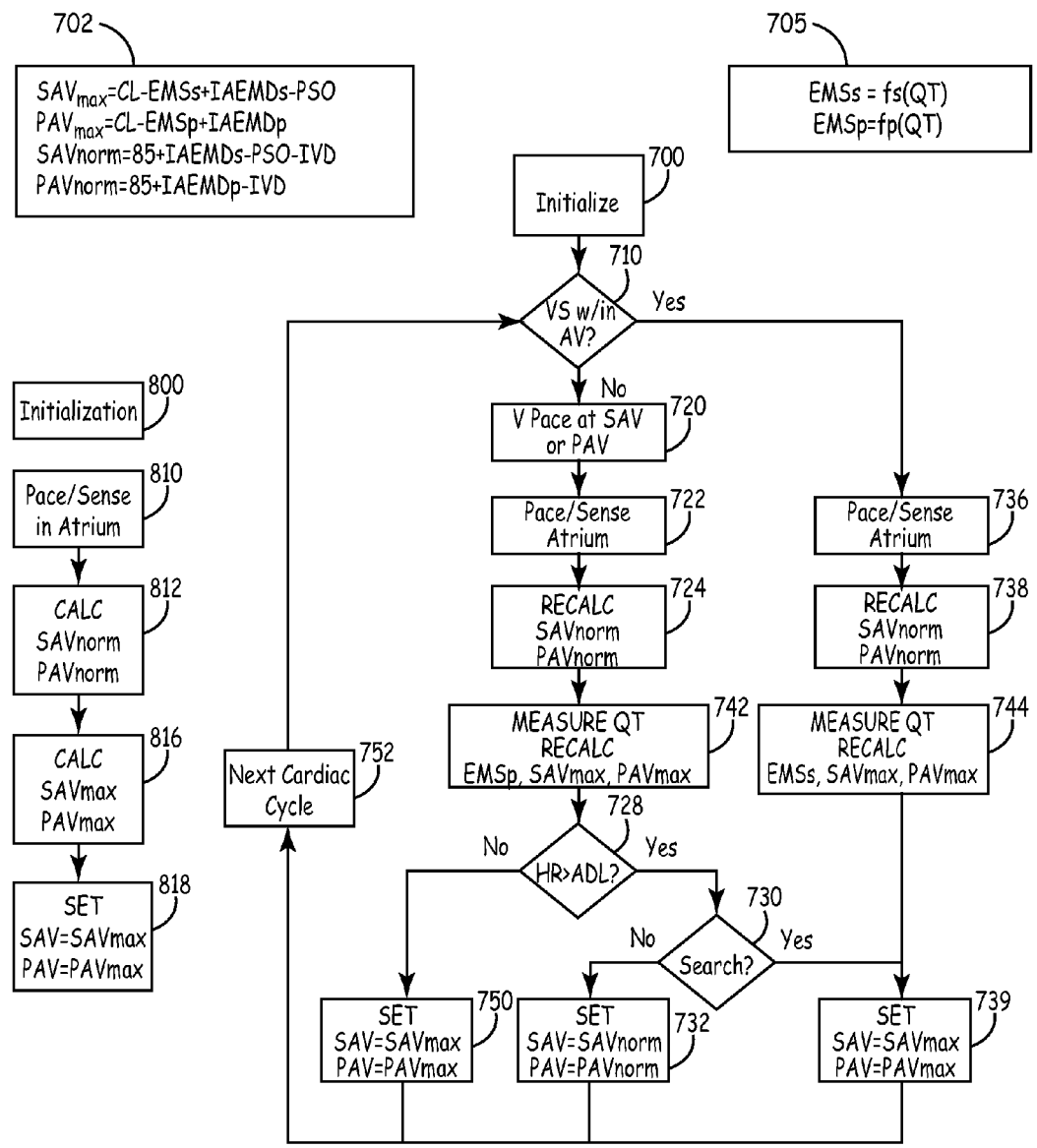

FIG. 15 is a flowchart illustrating a process wherein the EMS values are determined based upon QT intervals, as described herein. As most of the steps are the same or similar to those indicated in FIG. 14, only those that are different will be described. Equations (705) replace those of (704). Specifically, EMSs and EMSp are functions based upon the QT interval as described in detail above. The initialization process (800) is similar to that of FIG. 14, but step (814) is eliminated as resting EMS is not measured. As before, the variables are recalculated for each cardiac cycle. For initialization (800), the process may utilize one of two methods. In the first, multiple cardiac cycles pass and in at least one, ventricular pacing is delivered and in at least one ventricular pacing is withheld. Thus, measured values for all of the variables in (702) and (705) are obtained. In the second method, one or more cardiac cycles are utilized for initialization (800), but ventricular pacing is neither withheld nor "forced." As such, certain variables might not have measured initial values. If that is the case, default values are used in initialization (800) and actual values are obtained as the process proceeds and those values are utilized.

Steps (726) and (740) are replaced with steps (742) and (744) respectively. In step (742), the QT interval is measured, evaluated or otherwise obtained and provided to the device as a useable parameter. As ventricular pacing has occurred in the cardiac cycle, data for the EMSp is now available to update the EMSp parameter. Conversely, since no ventricular event was sensed, the EMSs cannot be updated and that variable retains the same value previously set.

In step (744), the QT interval is obtained. Here, a ventricular event was sensed so data is available to update the EMSs and that occurs. In both steps (742) and (744) the $SAV_{max}$ and $PAV_{max}$ values are recalculated; however, the EMS value will only change for one of those calculations depending upon whether the ventricular event was sensed or paced.

Figure 16:
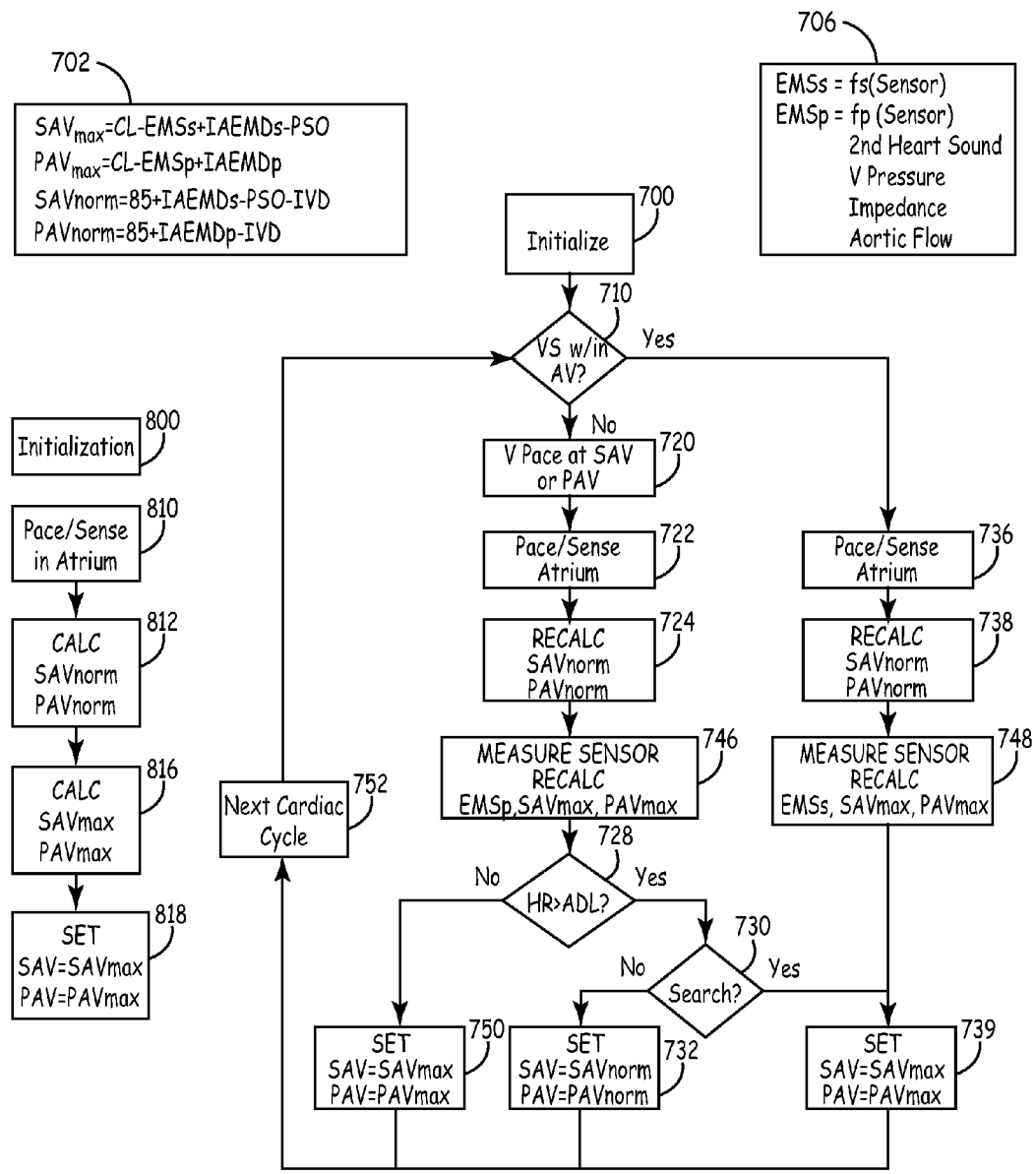

FIG. 16 is a flowchart illustrating a process wherein the EMS values are determined using sensor input. Once again, the steps are generally the same or similar to those indicated in FIGS. 14 and 15 so that only those that are different will be described. As indicated, the EMS formulas (706) are based upon sensor input that is indicative of a parameter associated with EMS, as described in detail above. For example, the sensor may be a microphone to pick up heart sounds, an impedance sensor to measure impedance values through the ventricle(s) to determine volume, a pressure sensor, or flow sensor. Steps (746) and (748) replace steps (742) and (744) respectively. The difference here being that sensor input is used to measure the appropriate EMS values, as opposed to QT intervals. The remainder of the flowchart includes the same steps.

The present invention has been described in the context of various embodiments. These embodiments are for illustrative purposes only and are not meant to be limiting, rather the spirit and scope of the invention may be broader than the specific embodiments provided which should not be limiting to the following claims.

The invention claimed is:

1. A method comprising:
measuring a resting electromechanical systole (EMSr) value at a resting heart rate (CLr);
calculating a current EMS value (EMSs) based upon a reduction from the EMSr of a proportional value of a difference between the CLr and a current heart rate (CL); and
setting a current AV interval in an implantable medical device having pacing capabilities, wherein the AV interval is equal to the CI-EMSs; and
further comprising calculating a current EMS value for ventricular pacing events (EMSp), wherein EMSp=EMSs+IVD where IVD is a value for interventricular conduction delay.

2. The method of claim 1, wherein the current AV interval includes a SAV value when atrial events are sensed and a PAV value when atrial pacing occurs and the SAV=CL-EMSs+IAEMDs-PSO, where IAEMDs is a value for interatrial electromechanical delay for sensed atrial events and PSO is a value for a P wave sense offset and the PAV=CL-EMSp+IAEMDp where the IAEMDp is a value for interatrial electromechanical conduction delay for paced events.

3. The method of claim 1 wherein the proportional value is 0.22.

4. A method for setting operating parameters for an implantable medical device (IMD) having pacing capabilities, the method comprising:
initializing a set of parameters, the parameters including:
a current heart rate (CL)
a resting heart rate (CLr);
a measured resting electromechanical systole (EMSr);
sensed electromechanical systole (EMSs), where EMSs=EMSr-((CLr-CL)×P) where P is a proportionality constant;
paced electromechanical systole (EMSp), where EMSp=EMSs+IVD where IVD is the interventricular conduction delay;
a non encroaching AV interval for cardiac cycles having sensed atrial events (SAVmax), where SAVmax=CL-EMSs+IAEMDs-PSO where IAEMDs is a value for interatrial electromechanical conduction delay for intrinsic atrial events and PSO is a value for a P wave sense offset;
a non-encroaching AV interval for cardiac cycles having paced atrial events (PAVmax), where PAVmax=CL-EMSp+IAEMDp where IAEMDp is a value for interatrial electromechanical conduction delay for paced atrial events;
setting an AV interval of the IMD to SAVmax for cardiac cycles having sensed atrial events and PAVmax for cardiac cycles having paced atrial events;
initiating the AV interval with occurrence of an atrial event;
sensing for ventricular activity during the AV interval;
delivering ventricular pacing upon the expiration of the AV interval absent sensed ventricular activity;
updating the value for CL based upon current heart rate; and
recalculating EMSs, EMSp, SAVmax, and PAVmax for a subsequent cardiac cycle based upon the updated CL.

5. The method of claim 4, further comprising:
initializing a SAVnorm parameter having a duration less than SAVmax and a PAVnorm parameter having a duration less than PAVmax;
determining if the CL is greater than an activities of daily living (ADL) rate, wherein the ADL rate is a value between a lower rate of the device and an upper rate of the device; and
setting the AV interval to SAVnorm and PAVnorm if the CL is greater than the ADL rate.

6. The method of claim 5, further comprising setting the AV interval to SAVmax and PAVmax if the CL is equal to or less than the ADL rate.

7. The method of claim 5, wherein determining if the CL is greater than the ADL rate only occurs in a given cardiac cycle if a ventricular pace is delivered.

8. The method of claim 4, wherein SAVnorm=MNV+IAEMDs−PSO−IVD and PAV norm=MNV+IAEMDp−IVD were MNV is a mean normal value for left side mechanical delay.

9. The method of claim 8, wherein P is about 0.22 and MNV is about 85 ms.

10. The method of claim 5, further comprising:
performing an intrinsic conduction check at periodic intervals while the CL is greater than then ADL rate by setting the AV interval to SAVmax and PAVmax from SAVnorm and PAVnorm for at least one cardiac cycle.

11. The method of claim 10, wherein the periodic intervals between conduction check increase in duration between subsequent conduction checks.

12. A method comprising:
storing a resting electromechanical systole (EMSr) value at a resting heart rate (CLr);
calculating a current EMS value (EMSs) based upon a reduction from the EMSr of a proportional value of a difference between the CLr and a current heart rate (CL); and
setting a current AV interval in an implantable medical device having pacing capabilities, wherein the AV interval is equal to the CI−EMSs; and
further comprising calculating a current EMS value for ventricular pacing events (EMSp), wherein EMSp=EMSs+IVD where IVD is a value for interventricular conduction delay.

13. A method for setting operating parameters for an implantable medical device (IMD) having pacing capabilities, the method comprising:
initializing a set of parameters, the parameters including:
a current heart rate (CL)
a resting heart rate (CLr);
a resting electromechanical systole (EMSr);
sensed electromechanical systole (EMSs), where EMSs=EMSr−((CLr−CL)×P) where P is a proportionality constant;
paced electromechanical systole (EMSp), where EMSp=EMSs+IVD where IVD is the interventricular conduction delay;
a non encroaching AV interval for cardiac cycles having sensed atrial events (SAVmax), where SAVmax= CL −EMSs+IAEMDs−PSO where IAEMDs is a value for interatrial electromechanical conduction delay for intrinsic atrial events and PSO is a value for a P wave sense offset;
a non-encroaching AV interval for cardiac cycles having paced atrial events (PAVmax), where PAVmax=CL−EMSp+IAEMDp where IAEMDp is a value for interatrial electromechanical conduction delay for paced atrial events;
setting an AV interval of the IMD to SAVmax for cardiac cycles having sensed atrial events and PAVmax for cardiac cycles having paced atrial events;
initiating the AV interval with occurrence of an atrial event;
sensing for ventricular activity during the AV interval;
delivering ventricular pacing upon the expiration of the AV interval absent sensed ventricular activity;
updating the value for CL based upon current heart rate; and
recalculating EMSs, EMSp, SAVmax, and PAVmax for a subsequent cardiac cycle based upon the updated CL.

* * * * *